(12) United States Patent
Hennings et al.

(10) Patent No.: US 8,409,183 B2
(45) Date of Patent: *Apr. 2, 2013

(54) ENDOVENOUS LASER TREATMENT GENERATING REDUCED BLOOD COAGULATION

(75) Inventors: David R. Hennings, Roseville, CA (US); David J. Fullmer, Roseville, CA (US); Craig Lindsay, Roseville, CA (US); Mitchel P. Goldman, Roseville, CA (US); Thomas Hennings, Roseville, CA (US); Monika G. Kiripolsky, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,750

(22) Filed: May 3, 2012

(65) Prior Publication Data
US 2012/0265179 A1    Oct. 18, 2012

Related U.S. Application Data

(63) Continuation-in-part of application No. 11/612,324, filed on Dec. 18, 2006, now abandoned.

(51) Int. Cl.
*A61N 5/067* (2006.01)
(52) U.S. Cl. .......... 606/15; 606/2; 606/3; 606/4
(58) Field of Classification Search ......... 606/2–5; 128/898; 607/88–90
See application file for complete search history.

(56) References Cited

U.S. PATENT DOCUMENTS

| | | |
|---|---|---|
| 4,233,991 A | 11/1980 | Bradley et al. |
| 4,854,320 A | 8/1989 | Dew et al. |
| 4,899,741 A | 2/1990 | Bentley et al. |
| 5,022,399 A | 6/1991 | Biegeleisen |
| 5,196,004 A | 3/1993 | Sinofsky |
| 5,207,672 A | 5/1993 | Roth et al. |
| 5,707,403 A | 1/1998 | Grove et al. |
| 5,789,755 A | 8/1998 | Bender |
| 5,810,801 A | 9/1998 | Anderson et al. |
| 5,820,626 A | 10/1998 | Baumgardner |
| 5,824,005 A | 10/1998 | Motamedi et al. |
| 5,885,274 A | 3/1999 | Fullmer et al. |
| 5,968,034 A | 10/1999 | Fullmer et al. |
| 5,976,123 A | 11/1999 | Baumgardner et al. |
| 5,984,915 A * | 11/1999 | Loeb et al. .......... 606/9 |

(Continued)

FOREIGN PATENT DOCUMENTS

| | | |
|---|---|---|
| WO | WO-92-17243 | 10/1992 |
| WO | WO-93-15664 | 8/1993 |

OTHER PUBLICATIONS

U.S. Appl. No. 10/335,176, filed Dec. 2 by Baumgardner et al.
US application No. 351,273 filed Jan. 3 by Hennings et al.
U.S. Appl. No. 10/699,212, filed Oct. 3 by Hennings et al.

(Continued)

*Primary Examiner* — Bill Thomson
*Assistant Examiner* — Jeffrey Lipitz
(74) *Attorney, Agent, or Firm* — Ray K. Shahani, Esq.; Kin Hung Lai

(57) ABSTRACT

Inducing thrombolysis of thermally induced thrombus occurring during endovenous ablation of varicose veins by introducing an optical fiber laser deliver device with optical fiber portion and with an energy emitting tip at its distal end into the varicosed vein to be treated, emitting pulsed, laser energy with sufficient energy to close and destroy varicose veins to the emitting tip of the optical fiber laser delivery device, thereby inducing laser thrombolysis of coagulated blood which accumulates at the energy emitting tip of the fiber when the fiber is caused to emit energy in the presence of uncoagulated blood and minimizing adverse effects associated with thermally induced thrombus within a varicose vein.

2 Claims, 38 Drawing Sheets

U.S. PATENT DOCUMENTS

| | | | |
|---|---|---|---|
| 6,014,589 | A | 1/2000 | Farley et al. |
| 6,015,404 | A | 1/2000 | Altshuler et al. |
| 6,028,316 | A | 2/2000 | Bender |
| 6,033,398 | A | 3/2000 | Farley et al. |
| 6,083,223 | A | 7/2000 | Baker |
| 6,117,335 | A | 9/2000 | Bender |
| 6,135,997 | A | 10/2000 | Laufer et al. |
| 6,139,527 | A | 10/2000 | Laufer et al. |
| 6,176,854 | B1 | 1/2001 | Cone |
| 6,197,020 | B1 | 3/2001 | O'Donnell, Jr. |
| 6,200,332 | B1 | 3/2001 | Del Giglio |
| 6,200,466 | B1 | 3/2001 | Bender et al. |
| 6,206,873 | B1 | 3/2001 | Paolini et al. |
| 6,224,593 | B1 | 5/2001 | Ryan et al. |
| 6,228,078 | B1 | 5/2001 | Eggers et al. |
| 6,258,084 | B1 | 7/2001 | Goldman et al. |
| 6,263,248 | B1 | 7/2001 | Farley et al. |
| 6,270,476 | B1 | 8/2001 | Santoianni et al. |
| 6,273,883 | B1 | 8/2001 | Furumoto |
| 6,273,885 | B1 | 8/2001 | Koop et al. |
| 6,290,675 | B1 | 9/2001 | Vujanic et al. |
| 6,346,105 | B1 | 2/2002 | Tu et al. |
| 6,361,496 | B1 | 3/2002 | Zikorus et al. |
| 6,398,777 | B1 | 6/2002 | Navarro et al. |
| 6,413,253 | B1 | 7/2002 | Koop et al. |
| 6,451,007 | B1 | 9/2002 | Koop et al. |
| 6,451,044 | B1 | 9/2002 | Naghavi et al. |
| 6,520,975 | B2 | 2/2003 | Branco |
| 6,626,899 | B2 | 9/2003 | Houser et al. |
| 6,638,273 | B1 | 10/2003 | Farley et al. |
| 6,761,826 | B2 | 7/2004 | Bender et al. |
| 2002/0049434 | A1 | 4/2002 | Teichmann |
| 2004/0010248 | A1 | 1/2004 | Appling et al. |
| 2008/0058908 | A1 | 3/2008 | Bornstein |
| 2011/0137230 | A1 | 6/2011 | Altshuler et al. |

OTHER PUBLICATIONS

U.S. Appl. No. 08/631,800, filed Apr. 1996 by Hennings et al.
U.S. Appl. No. 10/738,384, filed Dec. 3 by Hennings et al.
U.S. Appl. No. 11/131,577, filed May, 5 by Hennings et al.
U.S. Appl. No. 09/185,490, filed Jul. 2000 by Koop et al.
U.S. Appl. No. 09/135,330, filed Jul. 1998 by Koop et al.
U.S. Appl. No. 09/134,776, filed Aug. 1998 by Koop et al.
U.S. Appl. No. 10/160,579, filed May, 2 by Koop et al.
U.S. Appl. No. 10/031,154, filed Jan. 5 by Koop et al.
U.S. Appl. No. 08/482,208, filed Jun. 1995 by Hennings et al.
U.S. Appl. No. 11/612,324, filed Dec. 18, 2006 by Hennings et al.
Jacques; Skin Optics; Oregon Medical Laser Cent News; http://omlc.ogi.edu/news/jan98/skinoptics.html; Jan. 1998; 8 pages.
Chang et al.; Endovenous Laser Photocoagulation (EVLP) for Varicose Veins; Lasers in Surgery and Medicine 31:257-262 (2002); 6 pages.
Weiss et al.; Endovenous Closure of the Greater Saphenous Vein with Radio-frequency or Laser; Cosmetic Surgery Text 2003; 26 pages.
Weiss et al.; Controlled Radiofrequency Endovenous Occlusion Using a Radiofrequency Catheter Under Duplex Guidance to Eliminate Saphenous Varicose VeinUnique Reflux: A 2-Year Follow Up; American Society for Dermatologic Surgery, Inc. 2002; 5 pages.
Goldman et al.; Intravascular 1320nm Laser Closure of the Great Saphenous Vein: A 6-12 Month Follow-up Study; Dermatology/Cosmetic Laser Associates of La Jolla, Inc.; 28 pages.
Goldman; Endovenous Nd: YAG 1320nm Laser Treatment of the Greater Saphenous Vein: A Preliminary Study on 12 legs; Dermatology/Cosmetic Laser Associates of La Jolla, Inc,; 15 pa.
Goldman et al.; Endovenous 1064-nm and 1320-nm Nd: YAG Laser Treatment of the Porcine Greater Saphenous Vein; Cosmetic Dermatology; Feb. 2003; 4 pages.

* cited by examiner

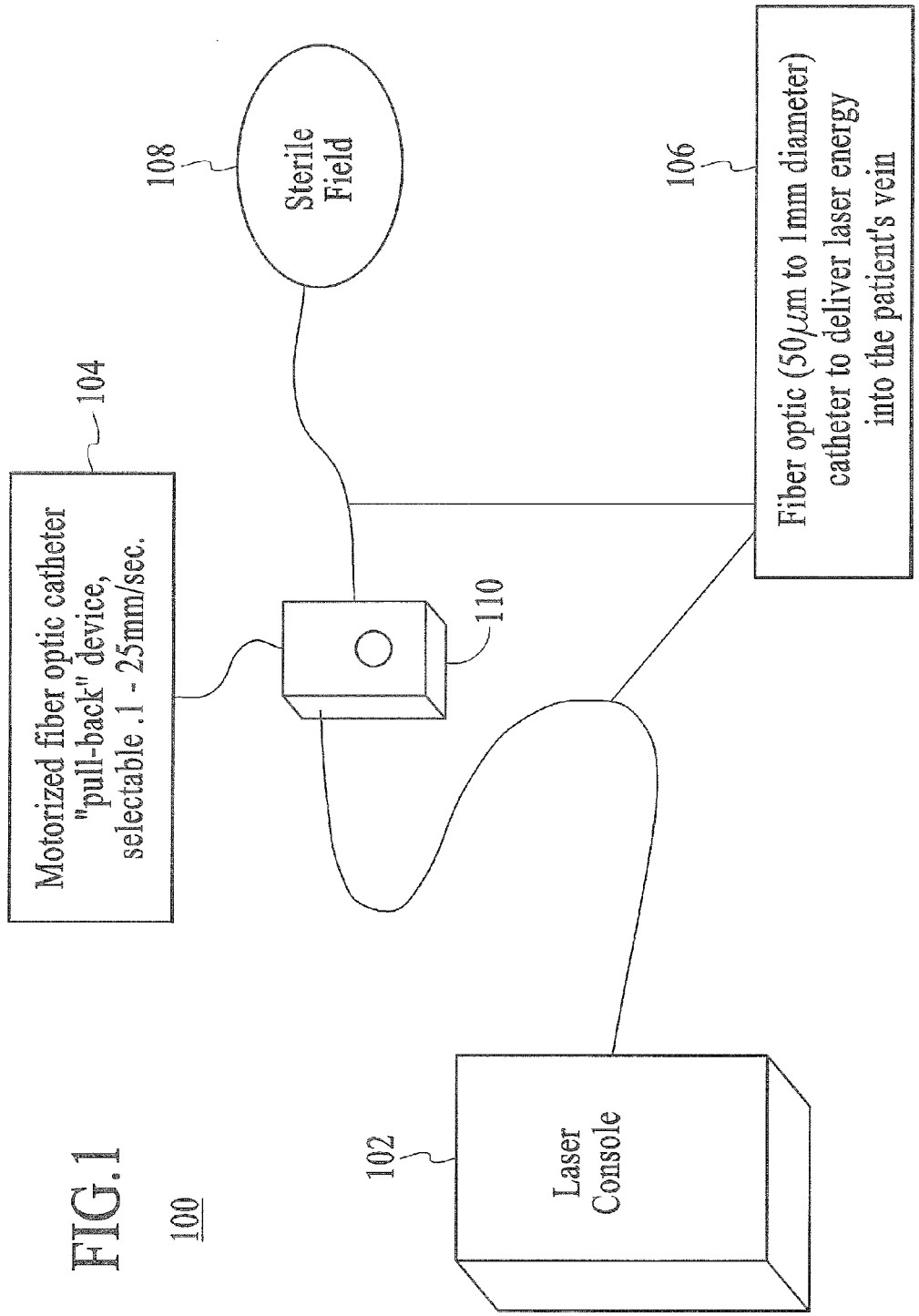

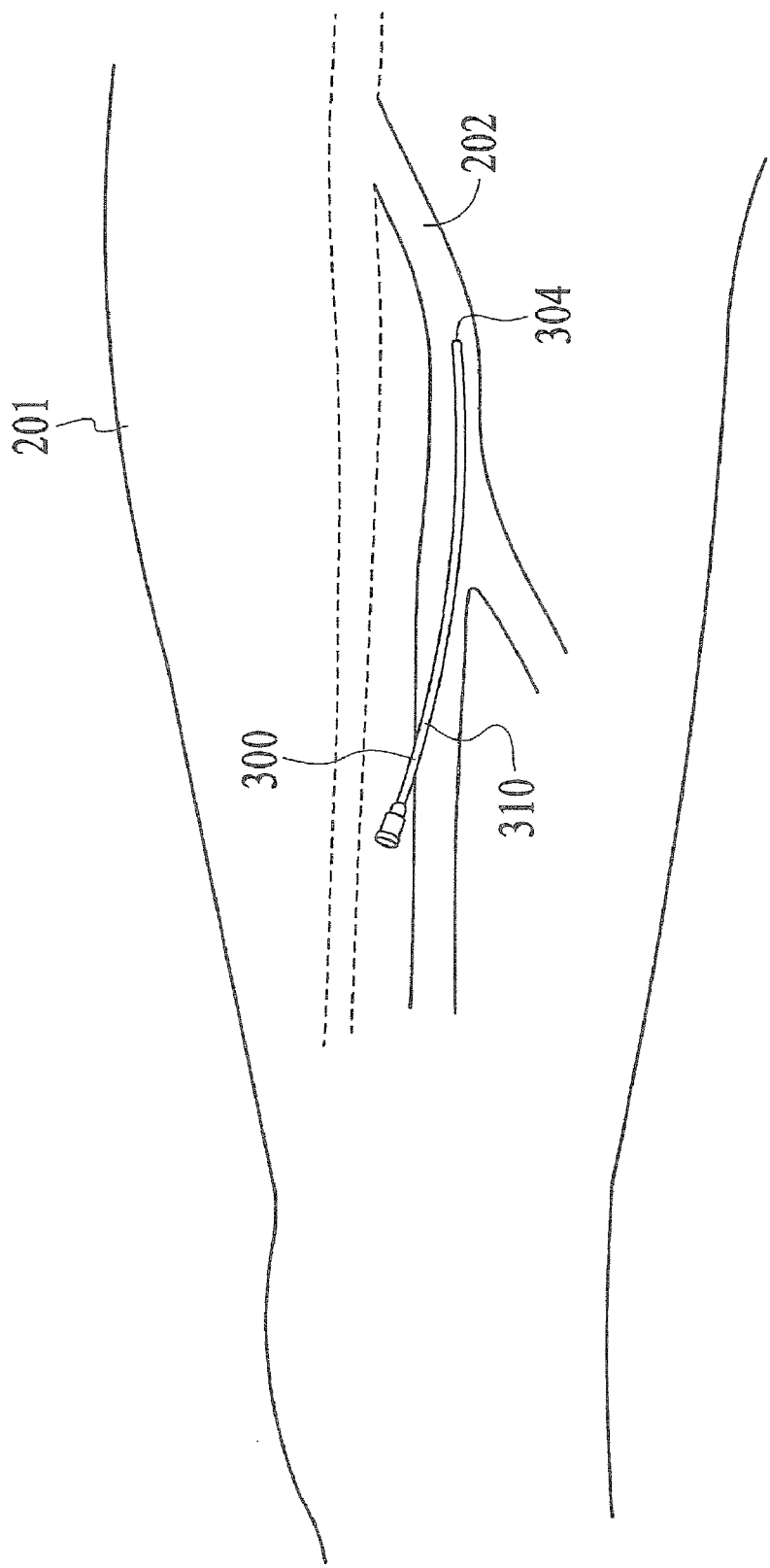

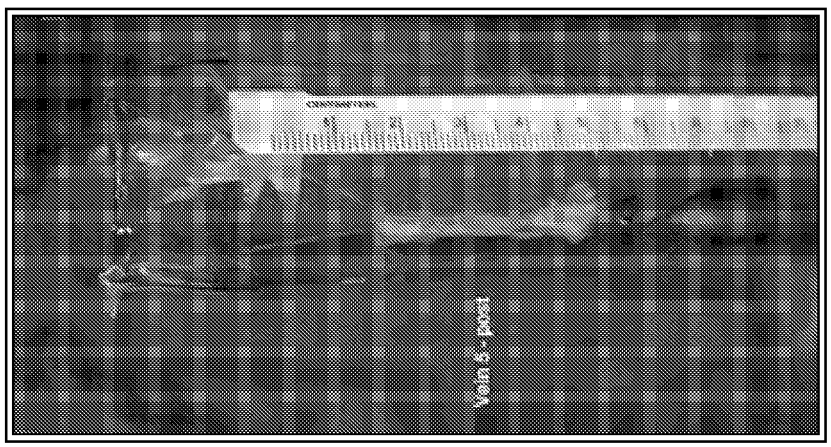
FIG. 32B Post - Laser
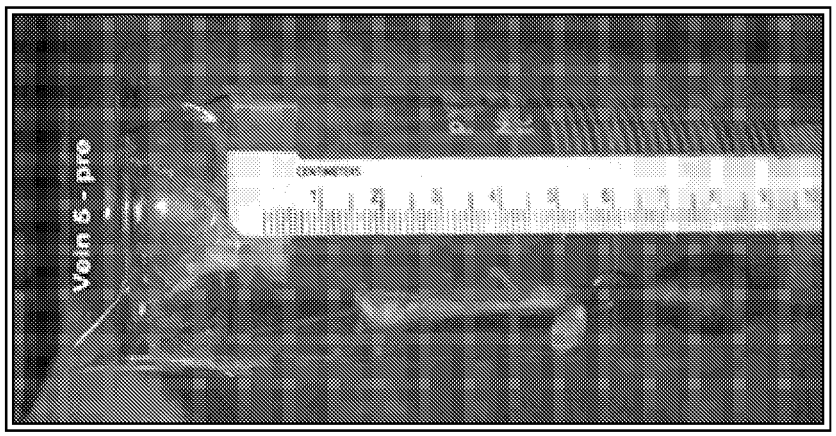
FIG. 32A Pre - Laser

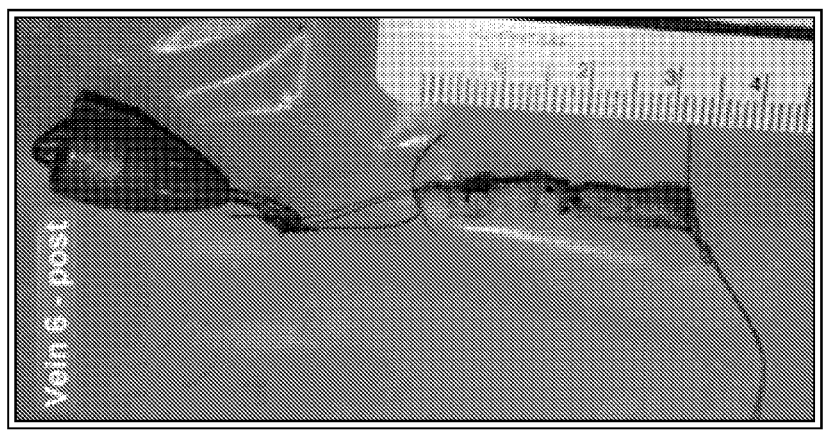
FIG. 33B  Post - Laser
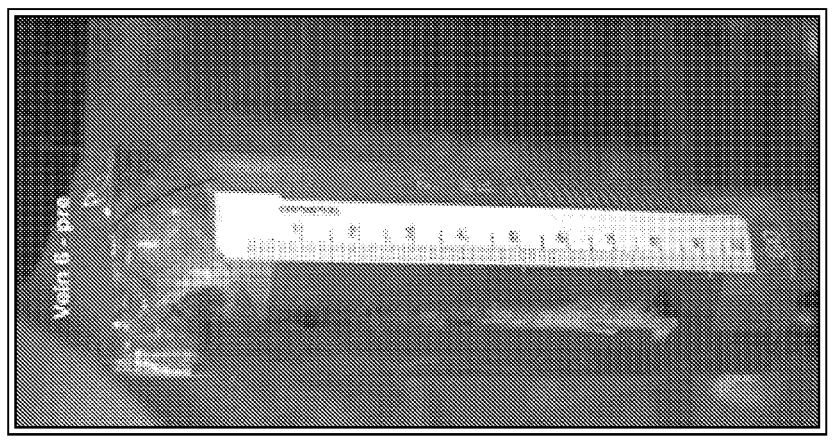
FIG. 33A  Pre - Laser

ENDOVENOUS LASER TREATMENT GENERATING REDUCED BLOOD COAGULATION

RELATED APPLICATION

This Application is a Continuation-In-Part of related pending U.S. patent application Ser. No. 11/612,324 filed Dec. 18, 2006 entitled ENDOVENOUS LASER TREATMENT GENERATING REDUCED BLOOD COAGULATION, and is related to U.S. patent application Ser. No. 10/982,504, filed on Nov. 4, 2004, and titled "ENDOVENOUS CLOSURE OF VARICOSE VEINS WITH MID INFRARED LASER", which application is a continuation-in-part of and claims the benefit of International Application Number PCT/US2003/035178, filed under the Patent Cooperation Treaty on Oct. 30, 2003, designating the United States of America, and titled "ENDOVENOUS CLOSURE OF VARICOSE VEINS WITH MID INFRARED LASER", which application claims the benefit of U.S. Provisional Patent Application Ser. No. 60/422,566 filed Oct. 31, 2002, entitled "ENDOVENOUS CLOSURE OF VARICOSE VEINS WITH MID INFRARED LASER", each of which applications are fully incorporated herein by reference in their entireties.

FIELD OF THE INVENTION

The present invention relates generally laser assisted method and apparatus for treatment of varicose veins and, more particularly, to improved laser devices and methods that reduce the amount of heat induced coagulum at the tip of the fiber optic treatment device and that improve the efficiency and safety of processes for delivering energy to the vein wall or other targeted tissue.

BACKGROUND OF THE INVENTION

Most prior techniques to treat varicose veins have attempted to heat the vessel by targeting the hemoglobin in the blood and then having the heat transfer to the vessel wall. Lasers emitting wavelengths of 500 to 1100 nm have been used for this purpose from both inside the vessel and through the skin Attempts have been made to optimize the laser energy absorption by utilizing local absorption peaks of hemoglobin at 810, 940, 980 and 1064 nm. RF technology has been used to try to heat the vessel wall directly but this technique requires expensive and complicated catheters to deliver electrical energy in direct contact with the vessel wall. Other lasers at 810 nm and 1.06 um have been used in attempts to penetrate the skin and heat the vessel but they also have the disadvantage of substantial hemoglobin absorption which limits the efficiency of heat transfer to the vessel wall, or in the cases where the vessel is drained of blood prior to treatment of excessive transmission through the wall and damage to surrounding tissue. All of these prior techniques result in poor efficiency in heating the collagen in the wall and destroying the endothelial cells.

In addition, blood coagulum that accumulates on the tip of the fiber optic energy delivery device is a significant problem associated with the prior art systems. The blood coagulum will often break off of the fiber and lodge in an early section of the treated vein, where it can thrombose and travel into the patient's venous circulation system. This is a serious complication referred to as Deep Vein Thrombosis (DVT) that, in the worst cases, is fatal to the patient. The blood coagulum can also block the energy coming out of the tip of the fiber and thereby reduce the effectiveness of the treatment. The only way to detect that fiber tip coagulation is occurring is to observe the lack of vein shrinkage under ultrasound, and then to remove the fiber to examine the tip. This is a common cause of non-closures or failures of the prior art endovenous treatments. The blood coagulum is able to absorb so much laser energy that it carbonizes and may explode, causing rupture of the vein wall. Navarro claims that this carbonized blood actually turns into a hot tip or conductive heating device that can transfer energy to the vein wall. In fact, it has been shown that the carbonized blood actually prevents any direct delivery of laser energy to the vein wall until the carbon explodes, which can cause vein wall perforation.

Blood coagulum that is caused by laser or RF heat delivery can also break off and remain inside the closed vein post treatment. Research has suggested that these regions of thrombus in a treated vein may not heal in a normal way and result in the vein staying patent or open. This is considered a treatment failure. When treating hand veins, these areas of heat induced thrombus left in an otherwise completely closed vein are cosmetically unattractive and need to be surgically punctured and drained post operatively to maintain a good result. Others report that Endovenous Heat Induced Thrombus (EHIT) is an expected post-procedure outcome, although one for which several treatment strategies are suggested. See Lowell S. Kabnick et al., "Endovenous Thermal Induced Thrombosis: Classification and Suggested Treatment," 2006 Int'l Vein Congress, Apr. 20-22, 2006. Of particular concern to physicians are instances when EHIT extends to close proximity or beyond the superficial-deep venous junction.

Baumgardner and Anderson teach the advantages of using the mid IR region of optical spectrum 1.2 to 1.8 um, to heat and shrink collagen in the dermis. The use of this wavelength region greatly reduces the occurrence of thrombus because of the lower hemoglobin absorption of these wavelengths, but since blood contains a significant amount of water it can still be heated with these water absorbing wavelengths and eventually cause a small thrombus.

The relevant references in the prior art teach the use of continuous or very long exposures of energy, such as bursts of about one second or more, up to continuous exposure. Peak power levels with these lasers run from about 10 to about 20 watts. These relatively long exposure times at these power levels are needed because the prior art laser wavelengths are not as efficiently coupled to the vessel wall and are instead absorbed in the blood or transmitted through the wall into surrounding tissue. It will be understood that methods taught in the prior art have been inefficient to such a degree that external cooling is needed on the skin surface to prevent burns. The high power and long or continuous exposure times associated with systems using high hemoglobin absorbing wavelengths have the result of creating a great deal of coagulum and thrombus. The coagulum and thrombus are effectively baked onto the tip of the fiber.

For example, Navarro et al., U.S. Pat. No. 6,398,777 issued Jun. 4, 2002, teaches a device and method of treating varicose veins that involves using laser energy whose wavelength is 500 to 1100 nm and is poorly absorbed by the vessel wall. Laser energy of wavelengths from 500 to 1100 nm will penetrate 10 to 100 mm in tissue unless stopped by an absorbing chromophore. See FIG. 5. Most of the energy used by this method passes through the vessel wall and causes damage to surrounding tissue. If sufficient blood is present in the vessel, a thrombus will form on the fiber tip that hardens and bakes on and eventually carbonizes completely over. This stops the delivery of energy to the blood (or anywhere else) until the carbon explodes, which can cause a vein wall perforation. Operative complications of this technique include bruising and extensive pain caused by transmitted energy and damage to surrounding tissue. Navarro teaches the use of peak powers of only 10 to 20 watts.

However, this technique does appear to be clinically effective because the blood that remains in the vein after compression absorbs the 500 to 1100 nm energy. 500 to 1100 nm light is absorbed in less than 1 mm in the presence of hemoglobin. See FIG. 5. This blood heats up and damages the vein wall by conduction, not by direct wall absorption as described by Navarro.

This prior art technique is also poorly controlled because the amount of residual blood in the vein can vary dramatically. During an actual procedure using 500 to 1100 nm lasers it is possible to see the effects of blood absorption of the energy. At uncontrolled intervals white flashes will be seen indicating places of higher blood concentration. The blood can boil and explode in the vessel causing occasional perforation of the vein wall and unnecessary damage to healthy tissue.

In places without residual blood the laser energy has no absorbing chromophore and will be transmitted through the wall without causing the necessary damage and shrinkage that occurs during the methods taught herein.

Navarro states that the treatment device described must be in direct "intraluminal contact with a wall of said blood vessel." This is necessary because the 500 to 1100 nm laser cannot penetrate any significant amount of blood, even though it requires a thin layer of blood to absorb and conduct heat to the vessel wall. This is very difficult to achieve and control.

Navarro also describes the delivery of energy in long exposure bursts of one second or more with very low peak powers. This is required using the described technique because Navarro describes no means for uniformly controlling the rate of energy delivered. Navarro teaches a method of incrementally withdrawing the laser delivery fiber optic line while a low peak power laser burst is delivered. In clinical practice this is very difficult to do and results in excessive perforations and complications. The Navarro laser device does not contain any power supply or control electronics or software to produce very short, high peak power, pulsed laser outputs as described herein. Instead, the Navarro device and other prior art diode lasers depend on a mechanical footswitch device to turn the laser energy emission on and off.

Closure of the greater saphenous vein (GSV) through an endolumenal approach with radiofrequency (RF) energy has also been achieved. The RF energy is delivered very slowly in continuous mode only and has caused a significant amount of coagulation or thrombus at the cathode tip. Many procedures need to be stopped and the catheter removed and cleaned of coagulum before proceeding.

RF energy can be delivered through a specially designed endovenous electrode with microprocessor control to accomplish controlled heating of the vessel wall, causing vein shrinkage or occlusion by contraction of venous wall collagen. Heating is limited to 85 degrees Celsius avoiding boiling, vaporization and carbonization of tissues. In addition, heating the endothelial wall to 85 degrees Celsius results in heating the vein media to approximately 65 degrees Celsius which has been demonstrated to contract collagen. Electrode mediated RF vessel wall ablation is a self-limiting process. As coagulation of tissue occurs, there is a marked decrease in impedance that limits heat generation. However, this process actually encourages coagulum formation by heat thrombosis. By limiting the temperature to non-ablative and non-boiling temperatures, one is generally assured that the blood will coagulate and not boil off as taught in the present invention.

Presently available lasers to treat varicose veins endolumenally heat the vessel by targeting the hemoglobin in the blood with heat transfer to the vessel wall. Lasers emitting wavelengths of 500 to 1064 nm have been used for this purpose from both inside the vessel and through the skin. Attempts have been made to optimize the laser energy absorption by utilizing local absorption peaks of hemoglobin at 810, 940, 980 and 1064 nm. The endovenous laser treatment of the present invention allows delivery of laser energy directly into the blood vessel lumen in order to produce endothelial and vein wall damage with subsequent fibrosis. It is presumed that destruction of the GSV with laser energy is caused by thermal denaturization. The extent of thermal injury to tissue is strongly dependent on the amount and duration of heat the tissue is exposed to.

One in vitro study model has predicted that thermal gas production by laser heating of blood in a 6 mm tube results in 6 mm of thermal damage. This study used a 940-nm-diode laser with multiple 15 Joules per second pulses to treat the GSV. Histologic examination of one excised vein demonstrated thermal damage along the entire treated vein with evidence of perforations at the point of laser application described as "explosive-like" photo-disruption of the vein wall. Since a 940 nm laser beam can only penetrate 0.03 mm in blood, the formation of steam bubbles is the probable mechanism of action. See T. M. Proebstle et al., "Thermal Damage of the Inner Vein Wall During Endovenous Laser Treatment: Key Role of Energy Absorption by Intravascular Blood," Dermatol Surg 28:7:July 2002.

Patients treated with prior art methods and devices have shown an increase in post-treatment purpura and tenderness. See, e.g., Edward G. Mackay et al., "Saphenous Vein Ablation," Endovascular Today, March 2006, pp. 45-48. Most patients do not return to complete functional normality for 2-3 days as opposed to the 1 day down-time with RF energy-based methods for treating the GSV. Since the anesthetic and access techniques for the two procedures are identical, it is believed that non-specific perivascular thermal damage is the probable cause for this increased tenderness. In addition, recent studies suggest that low peak power laser treatment with its increased risk for vein perforation may be responsible for the increase symptoms with endovenous laser treatment (EVLT) vs. RF treatment. Slow, uncontrolled pull-back of the catheter is likely one cause for overheating and perforation of the vessel wall, as even the best surgeon may have difficulty retracting the fiber at exactly the correct speed to maintain a vessel wall heating temperature of 85 deg C. This technique prevents damage to surrounding tissue and perforation of the vessel.

Prior art endovenous lasers have typically used relatively large fiber optic catheters of about 600 μm core diameter. This size fiber is selected to maximize the amount of laser power that may be coupled into the fiber. Prior art diode lasers are difficult to focus to small spots in high power levels because each diode bar typically needs to be imaged separately into the fiber optic. This is much easier when a large core fiber with high Numerical Aperture is used.

Varicose veins are commonly treated with a fiber optic catheter and a laser to coagulate the vein wall. Thermally induced thrombus is common during endovenous ablation. Thrombus can absorb laser energy reducing efficiency of vein wall coagulation and can carbonize and explode causing vein wall perforations. Proximal thrombus can break off into the venous system and intravenous thrombus can mask non-closed segments. Pulsed mid-infrared lasers have been used since at least the 1980s for laser thrombolysis in the treatment of strokes.1 Lasers with pulse lengths from 10 nsec to 10 msec have been used to generate vapor bubbles that break up clots when they collapse. These same lasers will generate less thrombus in the presence of blood during an endovenous ablation procedure. Heating blood has been found to cause many changes in erythrocytes, such as cell shape modification, cell membrane rupturing, protein denaturation, aggregation, and blood gelation that can all possibly contribute to coagulum formation.2 Laser treatment also causes the development of fibrin through thermal alteration of fibrin complexes or proteolytic cleavage of fibrinogen3. Laser treatment of cutaneous vascular disease causes intravascular consumption of fibrin-promoting factors3. Determining the conditions for minimal coagulum formation can help to reduce rates of complications.

ADVANTAGES AND SUMMARY OF THE INVENTION

In a first aspect, the present invention includes methods and devices for increasing the safety and efficacy of endovenous laser treatment of varicose veins by providing reduced formation and controlled clearing of the coagulum at the tip of an endovenous fiber. These devices and methods provide a way to substantially prevent the formation of coagulum upon the fiber tip of an endovenous laser treatment device, and to clear the fiber tip of coagulum without causing carbonization and explosive disruption of the vein wall.

As noted above, residual blood coagulum on the optical fiber tip is a serious impediment to the use of lasers to treat varicose veins. It is not possible to remove all the blood from a vein prior to treatment. Techniques such as elevating the leg, using compression, inducing spasm of the vein and using large amounts of tumescent anesthesia can all reduce the amount of blood present but there will typically always be pockets of blood that the laser must penetrate through to get a good shrinkage and closure of the vein. The use of a non hemoglobin absorbing laser such as one operating at a wavelength of 1320 nm has greatly reduced the coagulum that accumulates on the fiber tip, but there are still some instances where enough blood exists and coagulum could form. This could occur in very large veins or at locations close to the SF Junction where the vein must stay open or is just beginning to need closure.

Laboratory experiments, including several described herein, have shown that blood coagulates on the fiber tip in direct proportion to the absorption of the laser energy by the hemoglobin, and that there is a threshold where enough energy is delivered to the blood surrounding the fiber tip in a short enough time period such that the blood does not coagulate on the fiber tip and it remains clear and clean.

The present methods utilize laser pulses that are substantially shorter than those taught in the prior art. For example, the present methods use shorter pulses of 5000 μsec or less, with peak power levels of about 1000 watts. These operational settings provide instantaneous boiling of the thrombus off of the fiber tip rather than the slow cooking taught by the prior art methods, such as the methods taught in the Navarro patent, which lead to baking the thrombus onto the fiber tip. The present exposure times are typically much less than 1% of the exposure times of the prior art methods. The tissue interaction at these very short exposure time intervals is substantially different and preferred in relation to that provided by the prior art methods.

Laboratory tests have been performed using laser wavelengths of 810 nm, 980 nm, 1064 nm, and 1320 nm of short and long pulse lengths and different energies per pulse and repetition rate. Identical fiber optic delivery devices connected up to these lasers were held in bovine blood preserved with heparin so that the fiber tips were at least 10 mm into the blood. At constant power levels of about 7 watts the formation of coagulum was measured for each laser system. 810 and 980 nm continuous exposure lasers formed coagulum of about 2 cc size at the fiber tip within a few seconds of exposure. This stopped energy from exiting the fiber until the blood charred and then exploded from overheating. The 1320 low energy per pulse laser took about 30 seconds of exposure to form coagulum and it did not explode with increased exposure. The 1320 laser with higher energy per pulse did not develop coagulum over the fiber emitting end no matter how long it was exposed to the blood. This demonstrated the self cleaning nature of the proper wavelength and pulse energy.

The laser parameters can be adjusted to the levels needed to self clean a fiber tip by adjusting the power supply electronics that control the laser. In particular, the Nd:YAG laser used in the foregoing experiments is a crystalline laser that can be pulsed in a manner such that very high peak powers can be produced to enable this self cleaning action of the fiber tip. Nd:YAG lasers are used in many industrial and medical applications where high energy pulses are needed to drill holes and cut tissue. Lasers described in prior art endovenous treatment methods, such as 810 and 980 Diode lasers, cannot be pulsed in this manner because the facets of the diode bars cannot handle the high peak energy levels.

In addition, the Nd:YAG laser that is preferably used in the methods described herein is relatively easy to couple into small fibers with relatively lower Numerical Apertures ("NA"). Small diameter, low NA fibers have a much higher energy density at the emitting tip of the fiber, which reduces the development of coagulum at the fiber tip. Energy density is the energy of a laser pulse divided by the area of the emitting core of the fiber tip. This value changes with the square of the fiber diameter. This principle will also apply to relatively larger core (e.g., 600 μm) fibers if the pulse length is short enough, but the effect is enhanced when smaller core (e.g., about 150 to about 365 μm) fibers are used.

The energy per pulse and pulse length can be controlled in a crystalline laser by adjusting the electrical current flowing through the flashlamp or pump source of the lasing cavity. This is done by selecting a pulse forming network of capacitance and inductance that naturally discharges into a flashlamp with the proper pulse length, or by switching a solid state device like an IGBT on and off at the correct timing. A flashlamp pumped laser is suitable for this application because a great deal of energy can be produced in the relevant time periods to produce tissue cleaning without charring. A crystalline laser typically has a relaxation oscillation time or natural pulse length of about 100 microseconds. This time period is suitable for cleaning of the coagulum from a fiber, although the suitable range is anywhere from less than 1 microsecond to over 5000 microseconds. If the pulse is too short, the energy will likely destroy the fiber tip. If the pulse length is too long, the heat delivered may conduct too far from the fiber tip with the result that the coagulum will simply char and bake on rather than ablate off. The proper pulse length to deliver the energy is related to the thermal relaxation time and heat conduction of the blood, and the volume of blood that the energy is absorbed in. The proper amount of energy must also be considered. If the energy per pulse delivered is too small, the blood volume will not reach the boiling point and will not clean off. If it is too high, the blood may boil too rapidly, causing large bubbles and loss of energy. The proper amount of energy per pulse is about 1 to 500 millijoules per pulse.

While some of the energy delivered by the fiber is used to prevent or eliminate coagulum formation, there still must be enough power delivered to perform the endovenous ablation procedure. From about 5 to about 7 watts of power are needed to properly ablate and close a typical vein. Clinical experiments have shown that the vein closure mechanism in a vein completely flushed of blood is not dependent on pulse width from 50 μsec to continuous and on pulse rate of from about 20 to about 100 hz as long as the power level is correct. The methods and devices described herein will optimize the energy and pulse width to reduce the formation of coagulum without affecting the energy needed for optimal closure.

Coagulum formation is also avoided with the use of a protected tip fiber. This type of fiber has a cladding or jacket material that extends all the way to the distal end of the fiber tip and prevents small amounts of energy from leaking out the side of the tip of the fiber that may cause coagulum to form. Prior devices have used plastic clad fibers with very high numerical aperture lasers that could cause the cladding to burn off and encourage the formation of coagulum and char. The present methods and devices include the use of all silica clad fibers that cannot burn away, and the use of spacers around the tip of the fiber that additionally prevent the formation of coagulum, as described in U.S. patent application Ser. No. 10/982,504, filed on Nov. 4, 2004, entitled "Endovenous Closure of Varicose Veins with Mid Infrared Laser", which application is hereby incorporated by reference in its entirety.

The present invention is a system for treatment of varicose veins. The system comprises an optical fiber adapted for insertion into and treatment of varicose veins, the optical fiber having proximal and distal ends and having an energy emitting tip at its distal end, the optical fiber also having a diameter between about 50 μm and about 1000 μm. The system further comprises a pulsed, laser energy source operatively coupled to said optical fiber with sufficient energy to close and destroy varicose veins, the laser energy source providing laser energy having a wavelength between about 0.5 μm and about 2.2 μm, the laser energy having a pulse length between about 1 μs and about 5000 μs, and the laser energy source pulsed at the rate of between about 5 Hz and about 1000 Hz producing pulses of energy of between about 1 mJ and about 500 mJ per pulse. Thus, the laser energy emitted from the energy emitting tip causes laser induced thrombolysis of coagulated blood which accumulates at the energy emitting tip of the fiber when the fiber is caused to emit energy in the presence of uncoagulated blood.

The present invention is also a method for endovenous ablation of varicose veins. The method comprises the following steps:

Introducing an optical fiber laser deliver device, with optical fiber portion having a diameter between about 50 μm and about 1000 μm and with an energy emitting tip at its distal end, into the varicosed vein to be treated;

Emitting pulsed, laser energy with sufficient energy to close and destroy varicose veins to the emitting tip of the optical fiber laser delivery device, the pulsed laser energy having a wavelength of between about 0.5 μm and about 2.2 μm and having a pulse length between about 1 μs and about 5000 μs, and being pulsed at the rate of between about 5 Hz and about 1000 Hz; and Inducing laser thrombolysis of coagulated blood which accumulates at the energy emitting tip of the fiber when the fiber is caused to emit energy in the presence of uncoagulated blood.

The present invention is also a method for laser induced thrombolysis of thermally induced thrombus occurring during endovenous ablation of varicose veins. The method comprises the following steps:

Introducing an optical fiber laser deliver device, with optical fiber portion having a diameter between about 50 μm and about 1000 μm and with an energy emitting tip at its distal end, into the varicosed vein to be treated;

Emitting pulsed, laser energy with sufficient energy to close and destroy varicose veins to the emitting tip of the optical fiber laser delivery device, the pulsed laser energy having a wavelength of between about 0.5 μm and about 2.2 μm and having a pulse length between about 1 μs and about 5000 μs, and being pulsed at the rate of between about 5 Hz and about 1000 Hz; and Inducing laser thrombolysis of coagulated blood which accumulates at the energy emitting tip of the fiber when the fiber is caused to emit energy in the presence of uncoagulated blood, thereby minimizing adverse effects associated with thermally induced thrombus.

A method for inducing thrombolysis of thermally induced thrombus occurring during endovenous ablation of varicose veins, the method comprising the steps of (1) introducing an optical fiber laser deliver device with optical fiber portion having a diameter between about 50 μm and about 1000 μm and with an energy emitting tip at its distal end into the varicosed vein to be treated, and (2) emitting pulsed, laser energy with sufficient energy to close and destroy varicose veins to the emitting tip of the optical fiber laser delivery device, the pulsed laser energy having a wavelength of between about 0.5 μm and about 2.2 μm and having a pulse length between about 1 μs and about 5000 μs, and being pulsed at the rate of between about 5 Hz and about 1000 Hz, thereby inducing laser thrombolysis of coagulated blood which accumulates at the energy emitting tip of the fiber when the fiber is caused to emit energy in the presence of uncoagulated blood and minimizing adverse effects associated with thermally induced thrombus formed within a varicose vein.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1 is a representative schematic block diagram of a preferred embodiment of the apparatus 100 of the present invention for performing an exemplary varicose vein closure procedure of the present invention.

FIG. 2C is a representative view showing the beginning of the introducer or dilator 300 for percutaneous access according to an embodiment of the method and apparatus of the present invention.

FIGS. 32A and 32B show portions of human vein suspended within cylinder of physiologic saline prior and post laser treatment using 1470 nm diode CW laser.

FIGS. 33A and 33B show portions of human vein suspended within cylinder of physiologic saline prior and post laser treatment using 2100 nm diode CW laser.

DETAILED DESCRIPTION OF THE PREFERRED EMBODIMENT

Figure 2A:
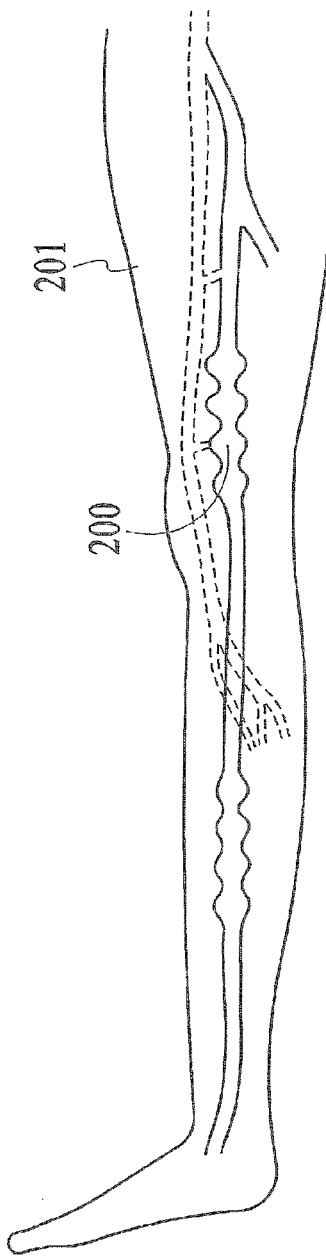
FIG. 2A is a representative view of varicosed veins 200 to be treated according to an embodiment of the method and apparatus of the present invention.

The description that follows is presented to enable one skilled in the art to make and use the present invention, and is provided in the context of a particular application and its requirements. Various modifications to the disclosed embodiments will be apparent to those skilled in the art, and the general principles discussed below may be applied to other embodiments and applications without departing from the scope and spirit of the invention. Therefore, the invention is not intended to be limited to the embodiments disclosed, but the invention is to be given the largest possible scope which is consistent with the principles and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

General Treatment Apparatus and Methods

FIG. 1 is a representative schematic block diagram of a preferred embodiment of the apparatus 100 of the present invention for performing a varicose vein closure procedure of the present invention. As shown, the system 100 includes a laser console 102, a motorized, fiber optic catheter "pull-back" machine 104, a fiber optic catheter or other laser delivery device 106 to deliver laser energy into the patient's vein, a sterile field 108, and a controller 110.

Figure 2B:
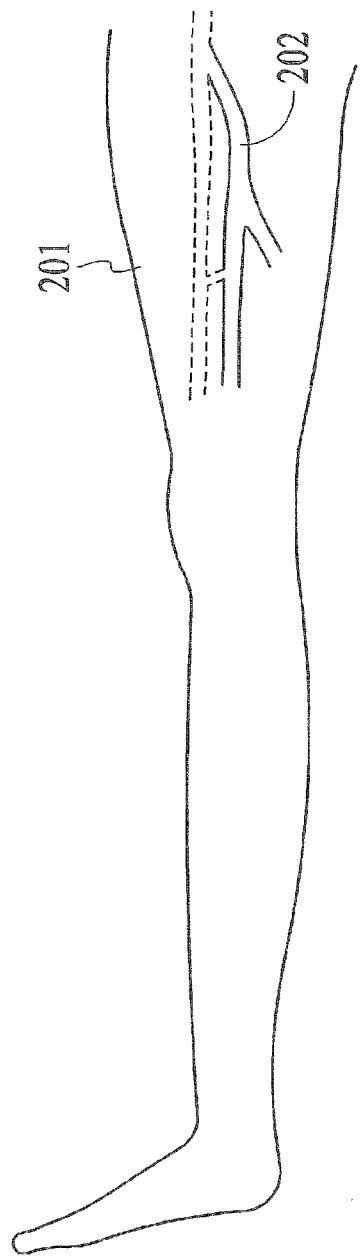
FIG. 2B is a representative-view of the GSV 202 to be treated according to an embodiment of the method and apparatus of the present invention.
Figure 2D:
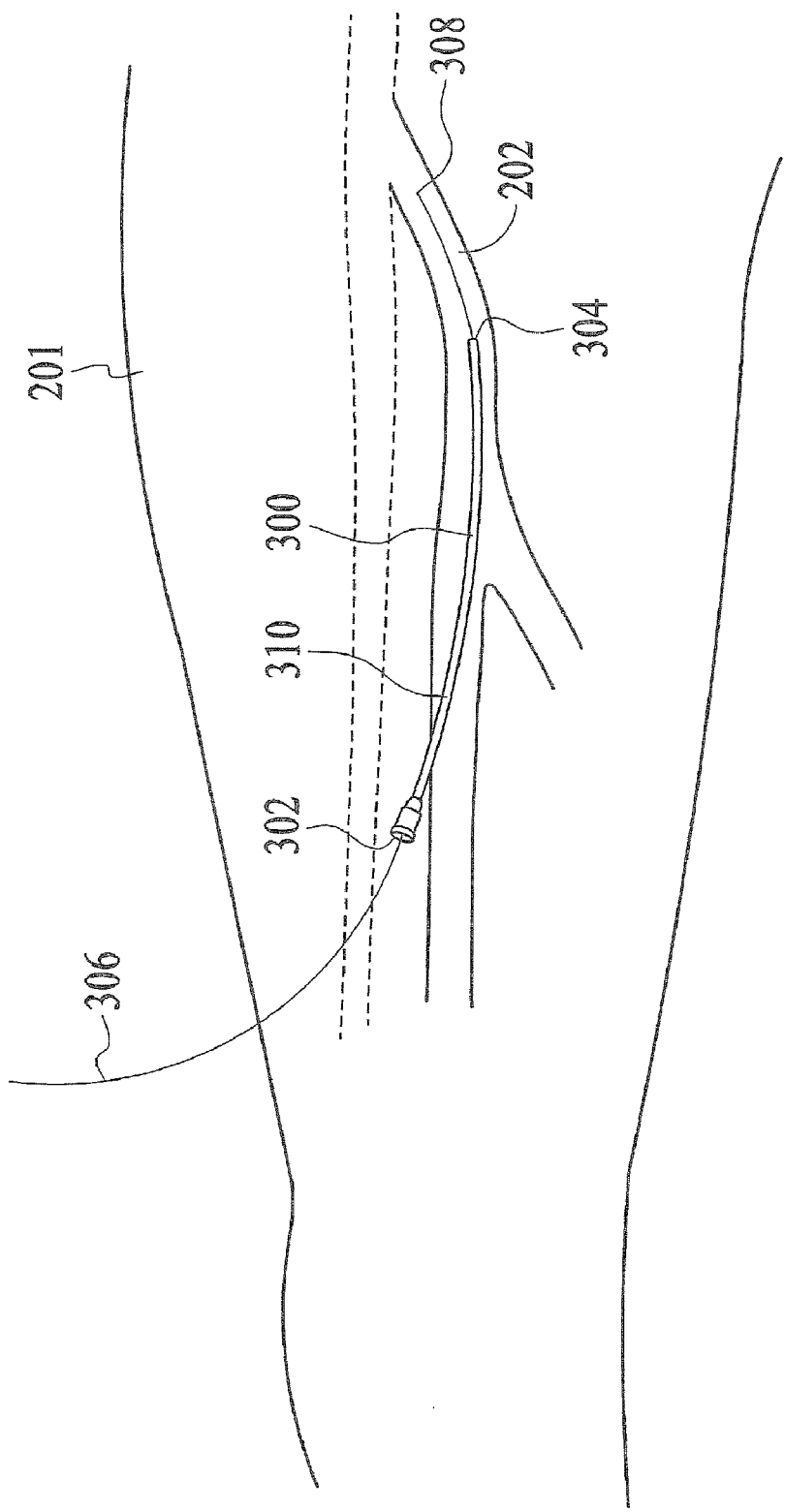
FIG. 2D is a representative view showing the use of the introducer or dilator 300 with the laser fiber 306 passing through the lumen 302 of the dilator 300 and into the GSV 202 according to an embodiment of the method and apparatus of the present invention.
Figure 2E:
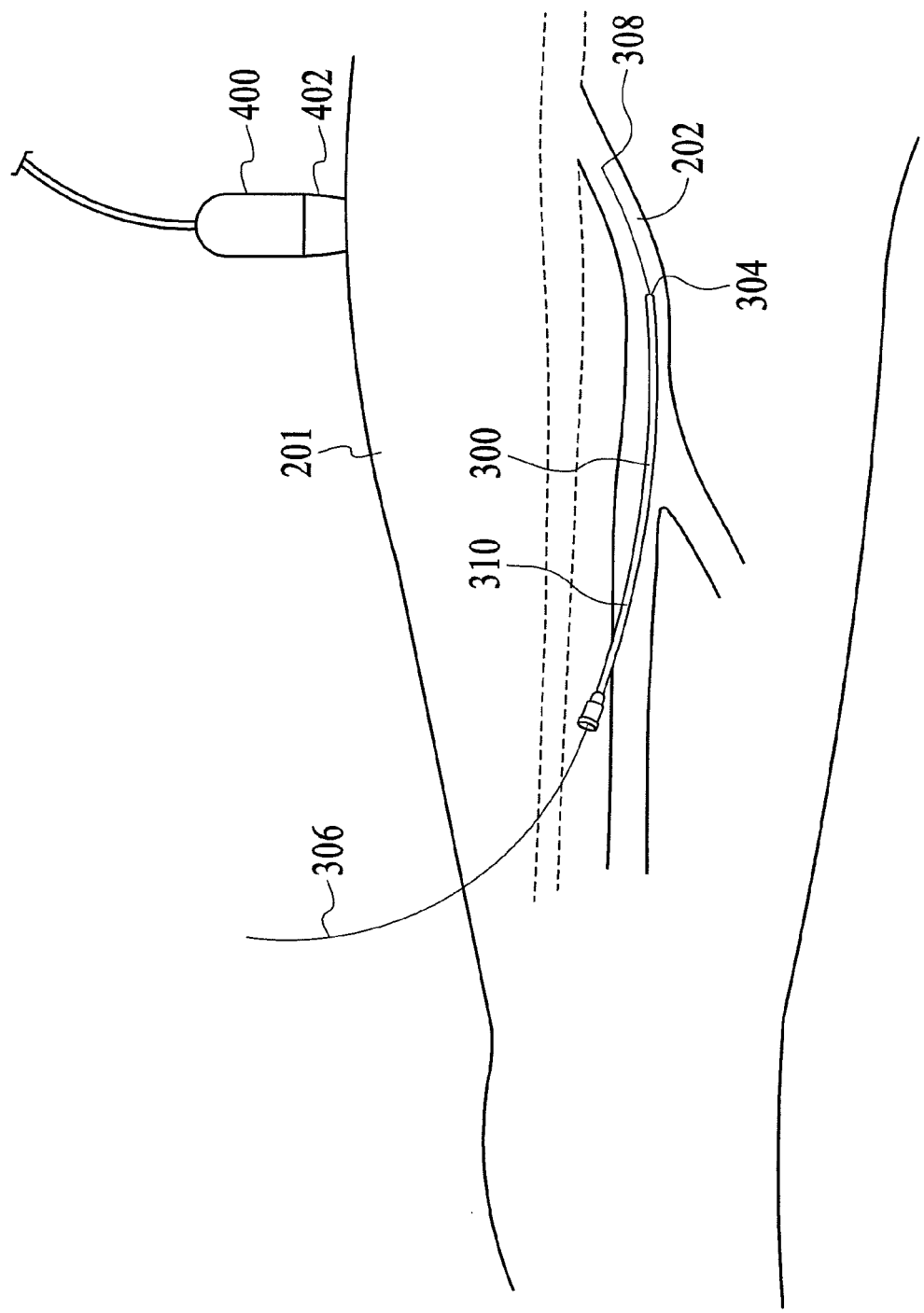
FIG. 2E is a representative view of the use of an ultrasound device 400 according to an embodiment of the method and apparatus of the present invention.

FIG. 2A is a representative view of varicosed veins 200 in the leg 201 of a human patient to be treated according to the methods and apparatus of the present invention. FIG. 2B is a representative view of the GSV 202 to be treated according to the methods and apparatus of the present invention. FIG. 2C is a representative view showing the percutaneous introduction of an introducer or dilator 300 into the GSV for percutaneous access according to the methods and apparatus of the present invention. FIG. 2D is a representative view showing the use of the introducer or dilator 300 with the laser fiber 306 passing through the lumen 302 of the dilator 300 and into the GSV 202 according to the methods and apparatus of the present invention. FIG. 2E is a representative view of the use of an ultrasound device 400 according to the methods and apparatus of the present invention.

Figure 3:
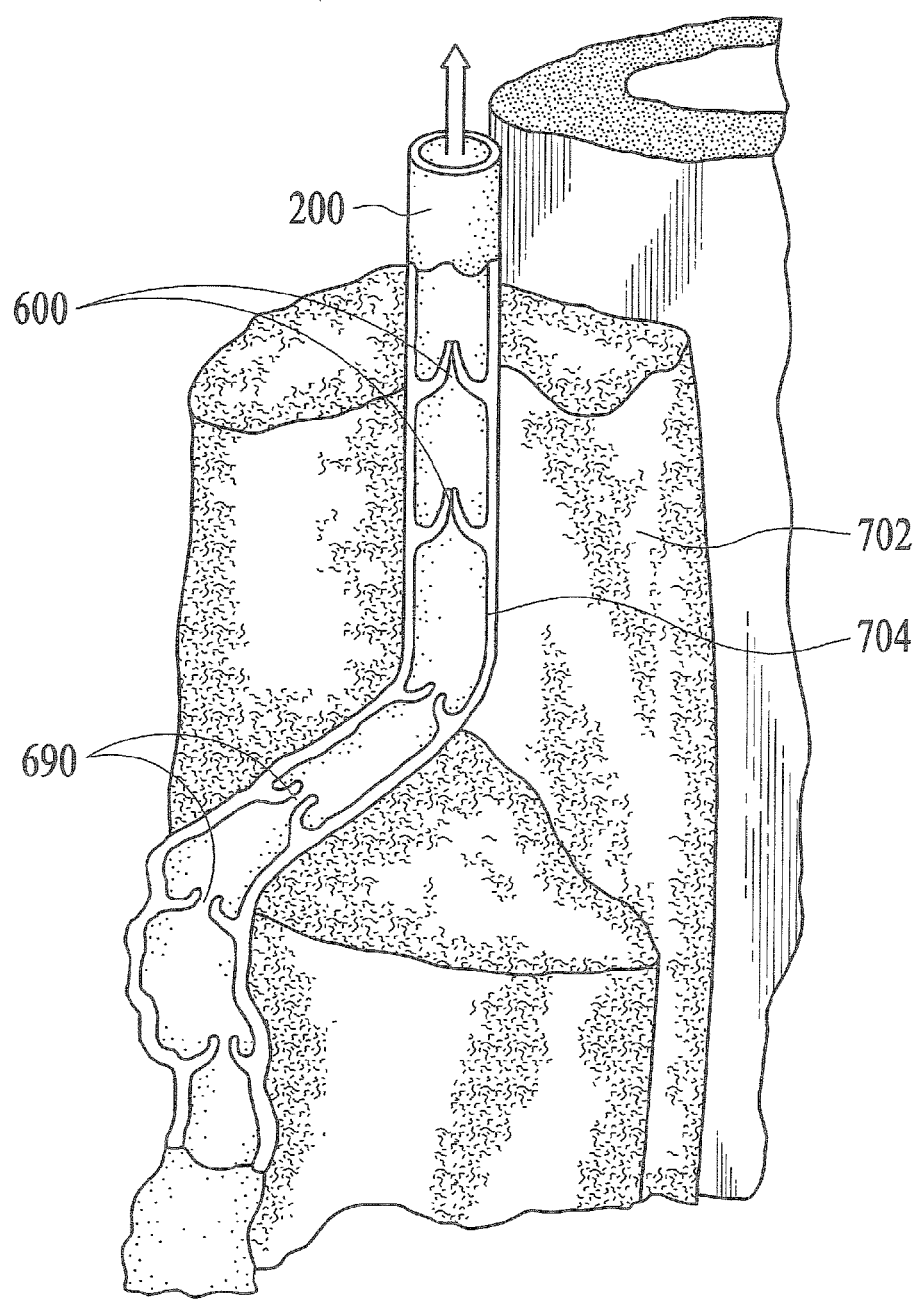
FIG. 3 is a is a representative view of a varicosed vein 200, showing prolapsed valves 690.

FIG. 3 is a is a representative view of a varicosed vein 200, showing intact valves 600 and prolapsed valves 690. The vein 200 has walls 704 and is surrounded by tissue 702.

Prior to treatment with the laser 102, as much blood as possible is preferably removed from the vessel 200. In a preferred embodiment, blood is removed by a combination of one or more of the following: external compression, massage, cooling, inducing spasms to the leg, and suction of the vein; the foregoing methods being described more fully in U.S. patent application Ser. No. 11/562,944, entitled "Preparation for Endovenous Laser Ablation", filed Nov. 22, 2006.

Turning to FIGS. 2A-E, a quartz or sapphire fiber optic 306 is inserted into the vein 200 via a 16 gauge needle or similar, or through a vein 200 which has been externalized through a 2-3 mm incision with a phlebectomy hook (not shown). The fiber 306 is preferably 275 to 365 um in diameter, but fibers from 50 um to 1 mm or more or less, could be used. The fiber catheter 300 is threaded through the length of the vein 200. The position of the fiber 306 within the vein 200 is noted by observing the red aiming beam of the laser 102 as it is emitted from the tip 304 of the catheter 300 and is visible through the skin. In addition, a duplex ultrasound device 400 (see FIG. 2E) or similar mechanism may be used to visualize the fiber tip 308 as well as the cannulated blood vessel 200 to determine vein wall contraction and closure. In a preferred embodiment of the method of the present invention, the catheter 300 must either be removed prior to pull-back, or be secured to the fiber 306 so that both the fiber 306 and the cannula or catheter 300 are retracted simultaneously.

The catheter 300 is preferably connected to a motorized pullback device 104 either inside or outside of the sterile field 108 of the patient. The procedure begins by turning the laser 102 on for a few seconds and then starting the pullback. The operational settings for the laser 102 and the speed of the pullback device 104 are determined by the criteria described below.

Figure 4:
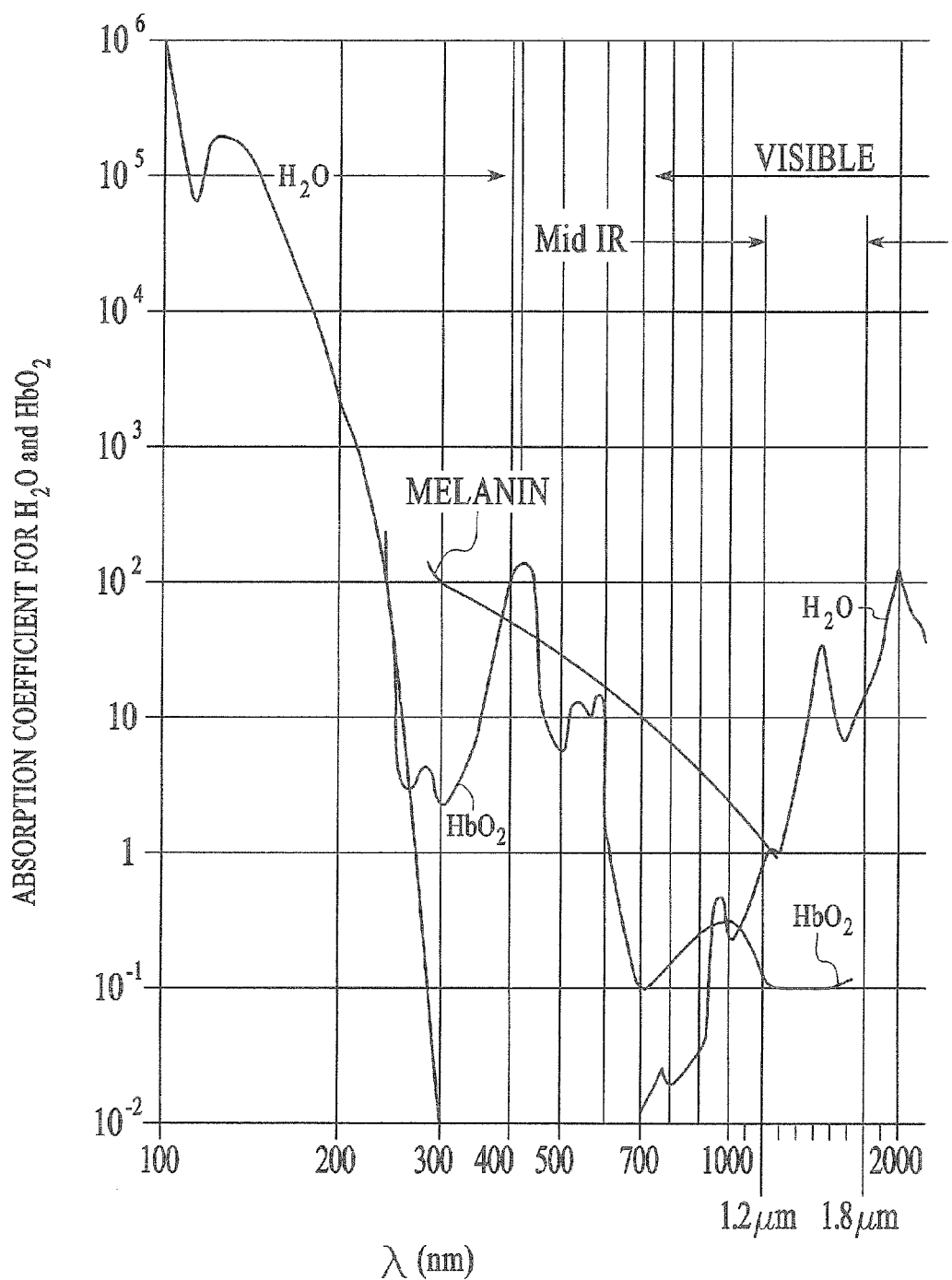
FIG. 4 shows curves for absorption coefficients of melanin, hemoglobin and water as a function of wavelength according to the preferred embodiment of the method and apparatus of the present invention.

Optical absorption curves presented by Baumgardner, Anderson, and Grove show that the primary absorbing chromophore in a vein for the 810, 940 and 1.06 um laser wavelengths is hemoglobin. See FIG. 4. When a vein is drained of blood and these lasers 102 are used, a great majority of the laser energy is transmitted through the vessel wall and heats surrounding tissue 702. The 1.2 to 1.8 um laser wavelengths, on the other hand, are ideally suited to penetrate the small amount of remaining blood in the vessel 200, but also are much more strongly absorbed in the vessel wall 704 by collagen. Most of the energy is concentrated in the wall 704 for heating and shrinkage and is not transmitted through to surrounding tissue 702. This dramatically increases the safety of the procedure. In addition, these laser wavelength are considered more "eye" safe than the 800 to 1.06 um lasers, decreasing the risk of eye damage to the doctor and others in the operating arena.

In particular, the Nd:YAG laser 102 or any other suitable, similar laser can be used. This laser 102 can operate at a wavelength of 1.32 um. Other lasers 102 such as Nd:YAP, ER:YAP, ER:YLF and others could be used to provide laser wavelengths in the 1.2 to 1.8 um region. These lasers 102 can be powered by optically pumping the laser crystal using a xenon or krypton flashlamp or laser diodes. They may be continuously pumped or pulsed using electro optical or acousto-optical shutters—or by pulsing the flashlamp itself. Lasers 102 in this wavelength region also include diode lasers that emit 1.2 to 1.8 um wavelengths directly, or fiber lasers that use a length of doped fiber optic as the lasing medium.

As noted above, FIG. 4 shows curves for absorption coefficients of melanin, hemoglobin and water as a function of wavelength according to the preferred embodiments of the methods and apparatus of the present invention. It will be observed in FIG. 4 that the region between about 550 nm to about 1060 nm shows high hemoglobin absorption and low water absorption, as is well known in the prior art technology. It will further be observed that the region between about 1200 nm to about 1800 nm shows low hemoglobin and higher water absorption, which is significant to the present methods.

Figure 5:
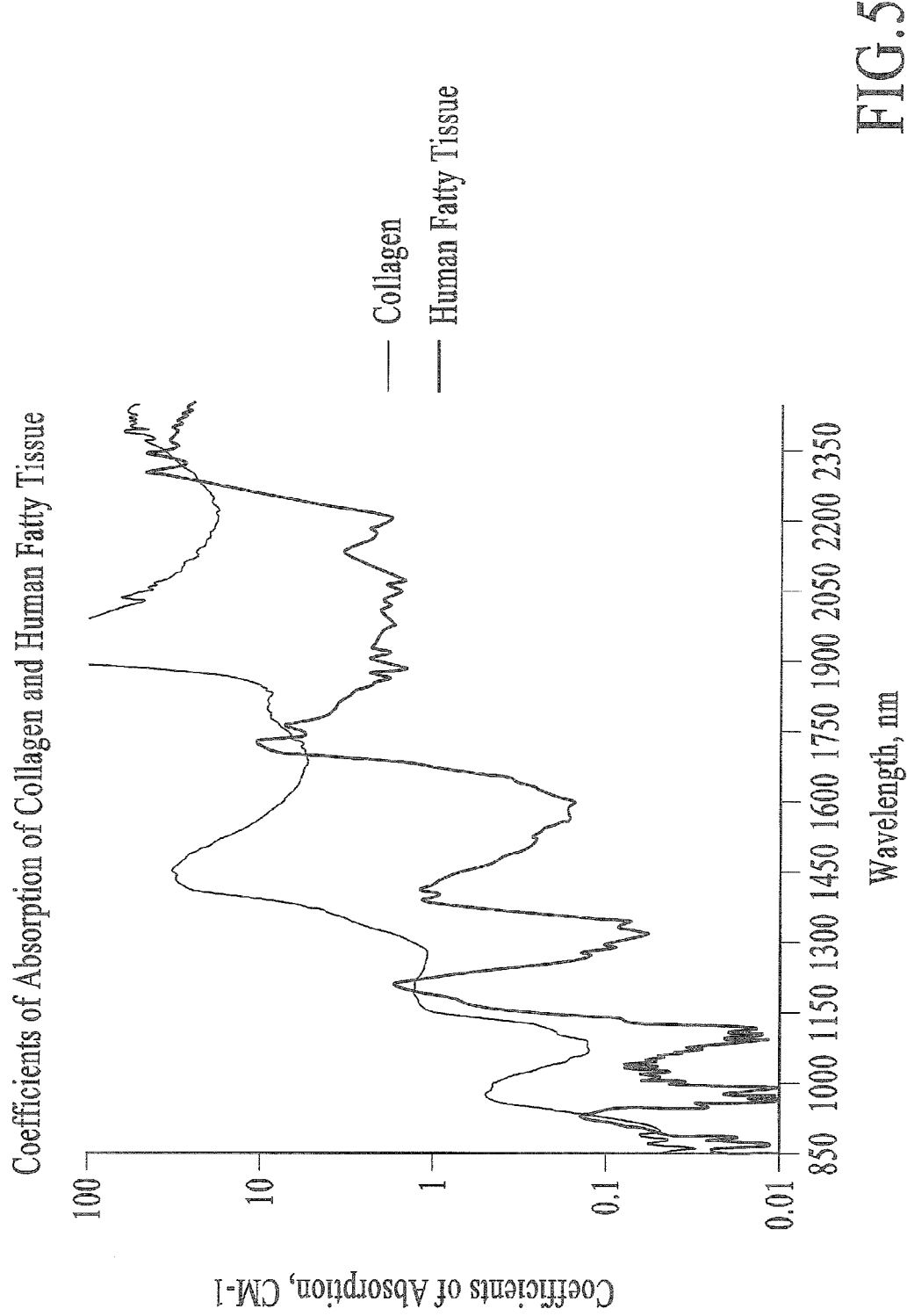
FIG. 5 is a graphical illustration showing curves for absorption coefficients of collagen and human fatty tissue as a function of energy wavelength.

FIG. 5 presents data comparing the coefficients of absorption of collagen and of human fatty tissue as a function of radiation wavelength. It is known that human fatty tissue has a different absorption spectra than collagen, and that there are wavelength windows in that spectra where it is possible to selectively target either fat or collagen with reduced impact on the other tissue. As can be seen in the Figure, in the ranges of from about 1300 um to about 1600 um, and from about 1900 um to about 2200 um, the absorption rate of collagen is much greater than that of human fatty tissue. This characteristic is further illustrated in FIG. 6, which presents the ratio of the coefficient of absorption of human fatty tissue to that of collagen as a function of wavelength. As noted on the Figure, the ranges of 1.3-1.8 nm and 1.9-2.2 nm represent "therapeutic windows" in which laser energy is highly absorbed in collagen relative to human fatty tissue. The devices and methods described herein take advantage of these properties by providing laser energy having wavelengths falling within these "therapeutic window" ranges. Within these ranges, the laser energy delivered will damage the target endothelial cells within the vein wall and will do little or no damage to the tissue surrounding the vein, including very little heating of the tissue that would otherwise cause pain, swelling or purpura in the dermis.

This effect is particularly pronounced when treating small vessels because they are in such close proximity to other parts of the dermis. It has been found that laser energy with wavelengths that have absorption depths of about 0.2 to about 2 mm are best for treating small (e.g., less than 2 mm diameter) vessels. The laser wavelength range that corresponds to these absorption depths is from about 1.3 to about 1.85 um, and from about 2.1 to about 2.6 um. On the other hand, larger vessels are best treated using laser energy at wavelengths that provide absorption depths of about 1 to about 3 mm to more uniformly heat all of the endothelial tissue without the risk of hot spots and potential perforation of the vessel wall. The laser wavelengths that correspond to these longer absorption depths are from about 1.14 um to about 1.38 um. The 1.32 um Nd:YAG laser satisfies each of these ranges.

Operation of System to Prevent Coagulum Formation

Figure 7:
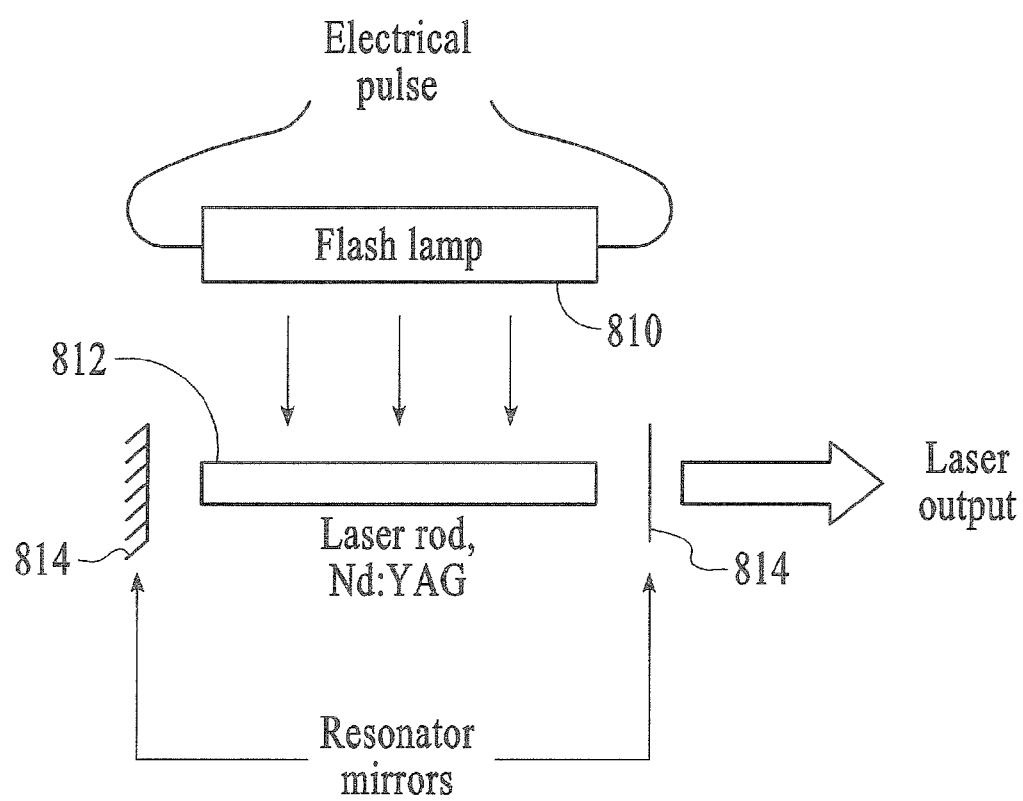
FIG. 7 is a schematic representation of a flashlamp pumped solid state laser.

FIG. 7 is a schematic representation of a laser that utilizes a flashlamp to pump the laser crystal. The use of a flashlamp is method of laser pumping that is generally known to those skilled in the art. It was one of the first methods used to produce laser energy, and is still in wide use because of it low cost and ability to produce large amounts of pulsed energy. The method described herein is a standard way to produce pulsed energy from a solid state laser such as an Nd:YAG or other crystalline medium laser. This method has been taught for many years for other applications, but is adapted to produce the type of laser output used by the methods described herein. The prior art endovenous treatment applications utilize continuous output semiconductor lasers that do not utilize flashlamp pumping. Semiconductor or diode lasers are activated by directly stimulating the medium with a low voltage direct current and, by design, cannot store and output giant energy pulses. The exemplary power supply described below is intended to illustrate a technique that is used to produce pulsed laser operation and to show that it is fundamentally different from continuous laser operation for the present methods.

A pulsed laser flashlamp 810 is a tube of glass or quartz that is sealed off at each end and contains a rare gas such as Xenon or Krypton. Electrical contacts through each end connect to an anode and a cathode inside the glass tube. When a high voltage is applied to the ends of the lamp it will discharge with a broad band white light. The lamp is placed in close proximity to the lazing crystal 812 so that the crystal absorbs the light energy. The crystal 812 stores this energy until a lazing threshold is reached when the energy is emitted through a process called stimulated emission. A set of aligned mirrors 814 around the crystal 812 allows selection of the wavelength and direction for this energy to propagate and to be coupled out of the crystal 812. Lasers that can be operated in giant pulse mode require lazing mediums that can store and then selectively release large amounts of energy. Solid state crystal lasers such as Nd:YAG lasers are optimal for this purpose. Semiconductor or diode lasers do not store significant amounts of energy and therefore can only be operated in continuous or very low energy per pulse modes.

Figure 8:
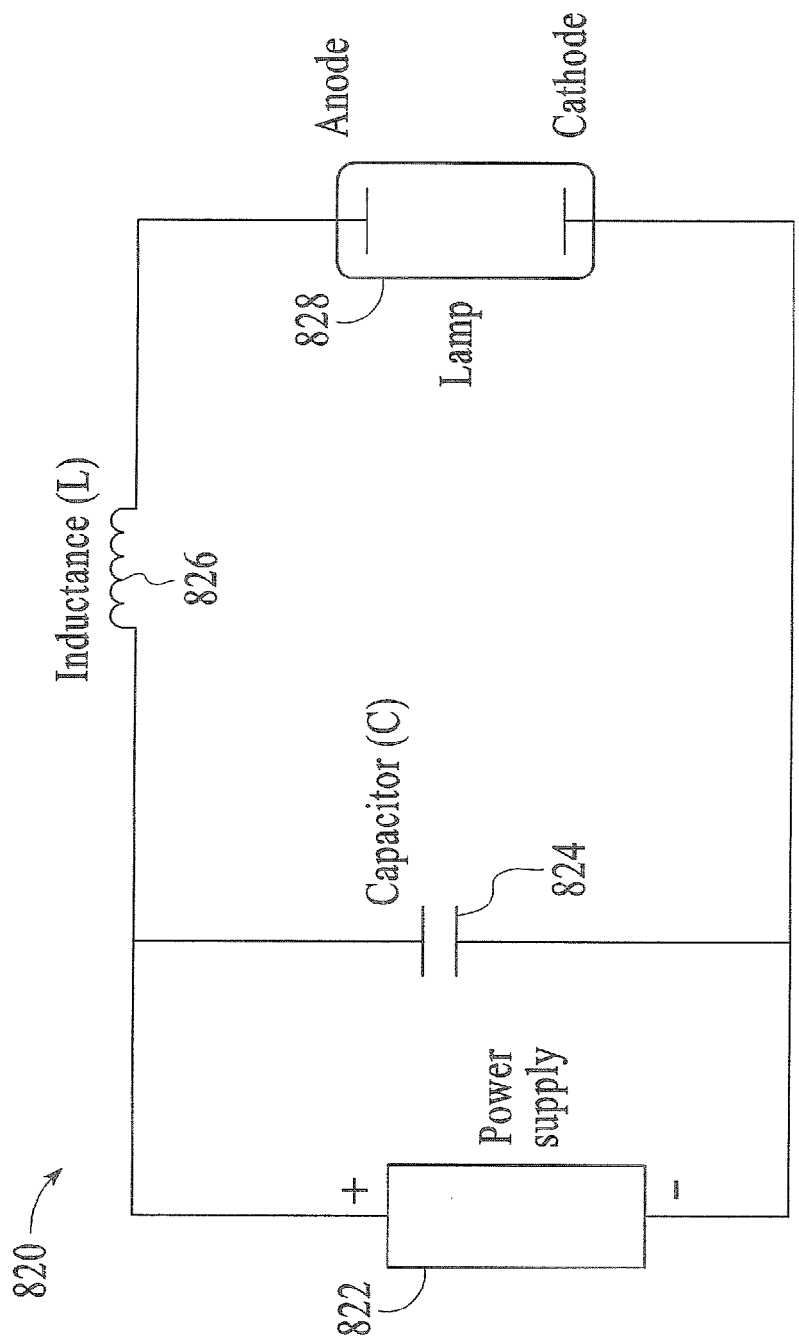
FIG. 8 is a schematic representation of an electronic pulse forming network used to produce pulsed laser output.

FIG. 8 is a schematic representation of a power supply 820 that can be used to pulse the flashlamp 810 to produce large energy pulses used in the methods described herein. A pulse lamp driving circuit typically contains a high voltage power supply 822, a main storage discharge capacitor 824, an inductor 826 to match lamp impedance and to control the pulse length, a lamp 828, and a triggering mechanism (such as a trigger transformer 852 described below in relation to FIG. 10) to initiate ionization in the gas in the lamp so that the main discharge current can flow through the lamp.

When the lamp 828 is non-ionized, it has a very high impedance and thus initially all the power supply current flows into the capacitor 824. If the voltage across the capacitor 824 or the trigger circuit reaches a value equal to the breakdown voltage of the lamp 828, ionization of the lamp 828 gas starts to occur and its impedance begins to fall. If sufficient charge is available, the plasma of ionized gas in the lamp 828 completely fills the bore and the lamp radiates energy in the form of light. Eventually all of the energy in the capacitor 824 is expended and the lamp 828 returns to a de-ionized state. This process can be repeated with a repetition rate that can be from a single isolated pulse to thousands of times every second. The energy discharges from the capacitor 824 through the flashlamp 828 with a pulse length that is determined by the values of the capacitor 824 and inductor 826 that has been selected for the pulse forming network. This pulse length can be shown to be: $T = \frac{1}{3}(LC)^{\frac{1}{2}}$, where L is the value of the inductor 826 and C is the value of the capacitor 824 in the network.

Figure 9:
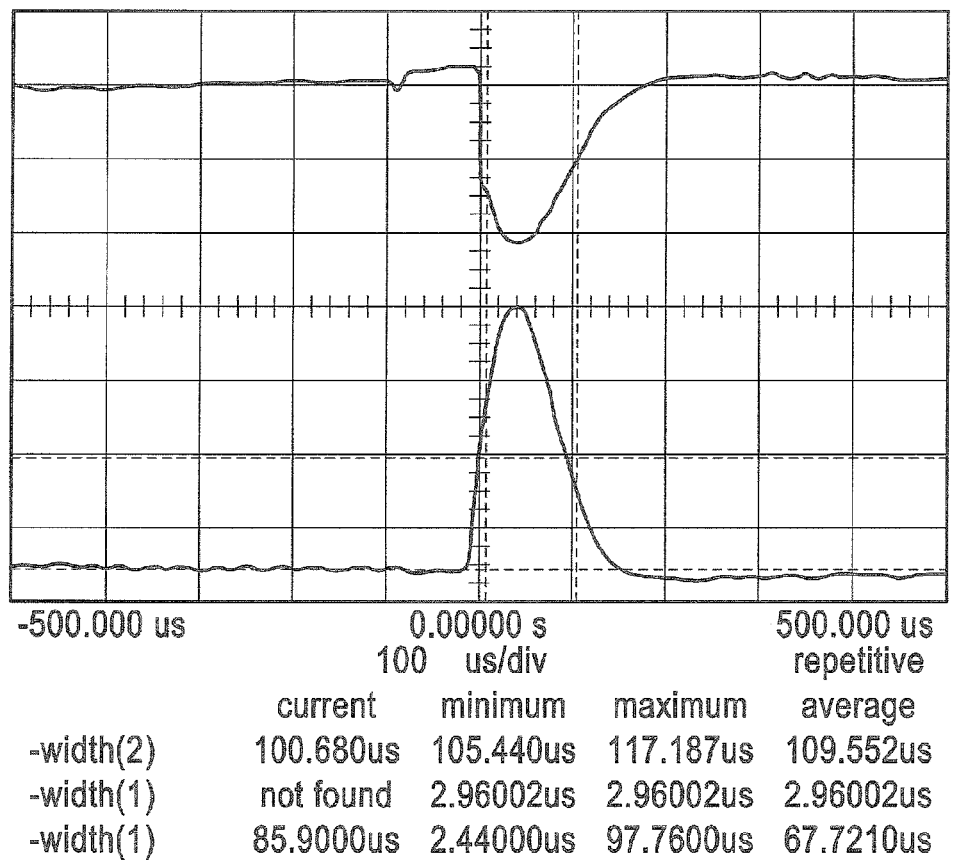
FIG. 9 is a photo of an oscilloscope readout illustrating a flashlamp pulse generated by the pulse forming network shown in FIG. 8.

Since the crystalline laser medium 812 will absorb white light and emit coherent monochromatic light in close agreement with the flashlamp pulse, proper selection of the flashlamp pulse length provides a method for controlling the giant pulse length of a solid state laser. It is controlled by the choice of the value of the main discharge capacitors 824 and inductors 826. However, the laser operates most efficiently when the flashlamp pulse length closely matches the fluorescent lifetime of the lasing medium and when the PFN (pulse forming network) matches the impedance of the lamp 828. For a typical Nd:YAG laser, this is about 200 μseconds. FIG. 9 is a photo of an oscilloscope readout illustrating an exemplary flashlamp pulse generated by the pulse forming network shown in FIG. 8.

The energy per pulse is determined by the energy stored in the main capacitor. This energy can be calculated to be: $E = \frac{1}{2}C(V)^2$, where V is the voltage that the capacitor is charged to. The output lasing energy will be a percentage of the flashlamp pump energy within the cooling constraints of the rest of the laser. For Nd:YAG crystals usually about 3% of the pump energy emits as coherent laser energy.

For the present endovenous laser treatment methods, typical values for the components are:
C=10 to 1000 μFarads
L=10 to 5000 μHenrys
V=200 to 2000 volts These values can produce pulse lengths from 3 to 800 μseconds, pump energies from 0.2 Joules to 2000 Joules per pulse, and laser output energies of 1 millijoules to 500 joules per pulse. These values have been shown to be effective in reducing the coagulum that develops at the tip of an endovenous laser fiber during treatment.

Figure 10:
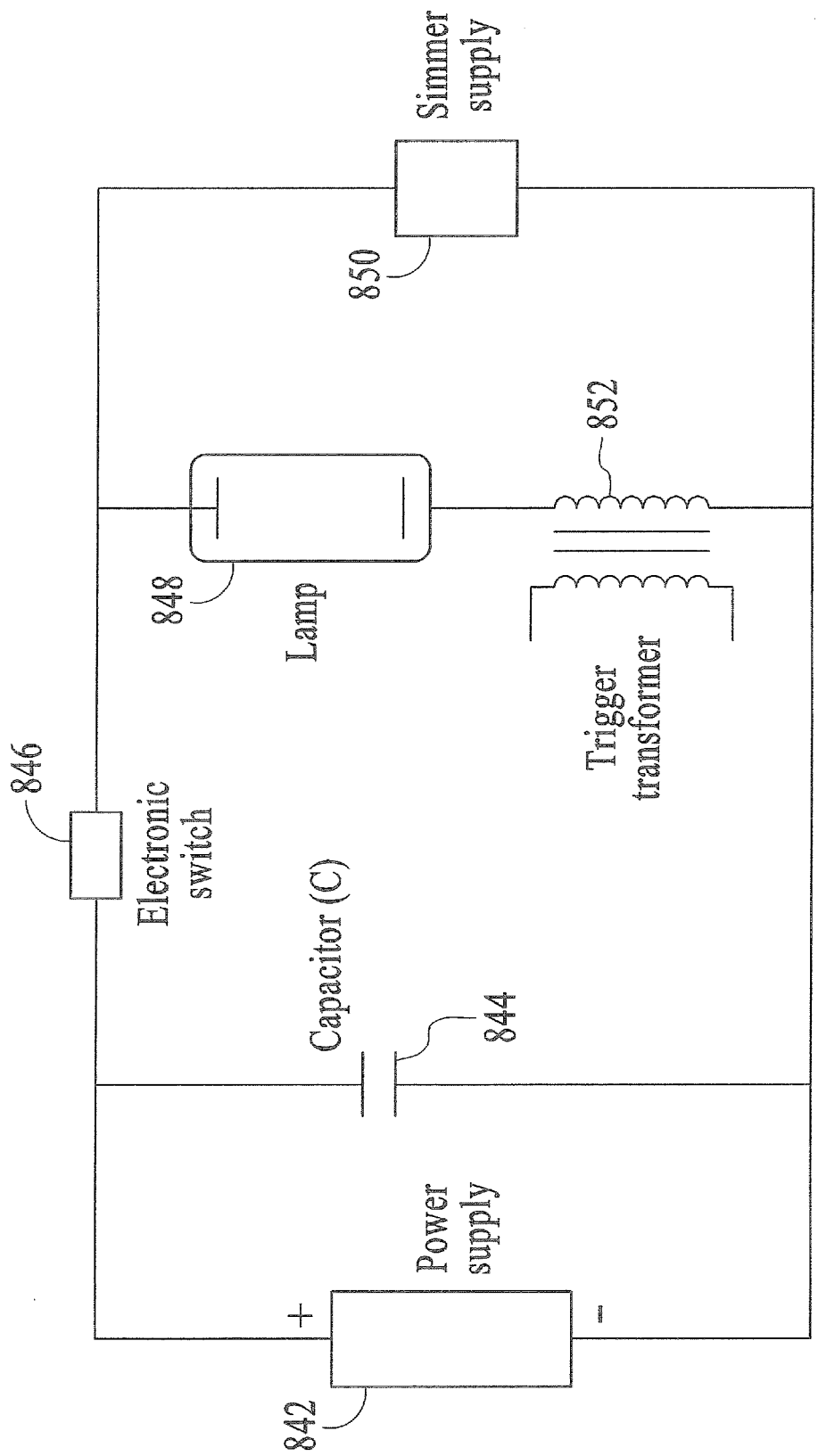
FIG. 10 is a schematic representation of an Isolated Gate Bipolar Transistor (IGBT) system suitable for producing pulsed laser output.

FIG. 10 illustrates an alternative electronic switching device referred to as an IGBT (Isolated Gate Bipolar Transistor), which can be used to generate pulsed energies in a flashlamp of the same values as a capacitive, inductive pulse forming network. The IGBT circuit includes a high voltage power supply 842, a main storage discharge capacitor 844, an electric switch 846, a lamp 848, a simmer supply 850, and a trigger transformer 852 to initiate ionization in the gas in the lamp so that the main discharge current can flow through the lamp. The device shown in FIG. 10 is usually operated at a fixed capacitor voltage and controls the energy discharge into the flashlamp by controlling the pulse length of the discharge. The IGBT device can shut off the current at any time, as opposed to a conventional transistor which cannot be controlled once it is turned on. A trigger transformer 852 is used to strike a high voltage arc in the flashlamp 848 to initiate a plasma current in the lamp of about 100 mamps. This plasma is maintained by a current limiting power supply called a simmer supply 850 and allows the discharge of a high current flashlamp pulse controlled by the IGBT 846.

Figure 11A:
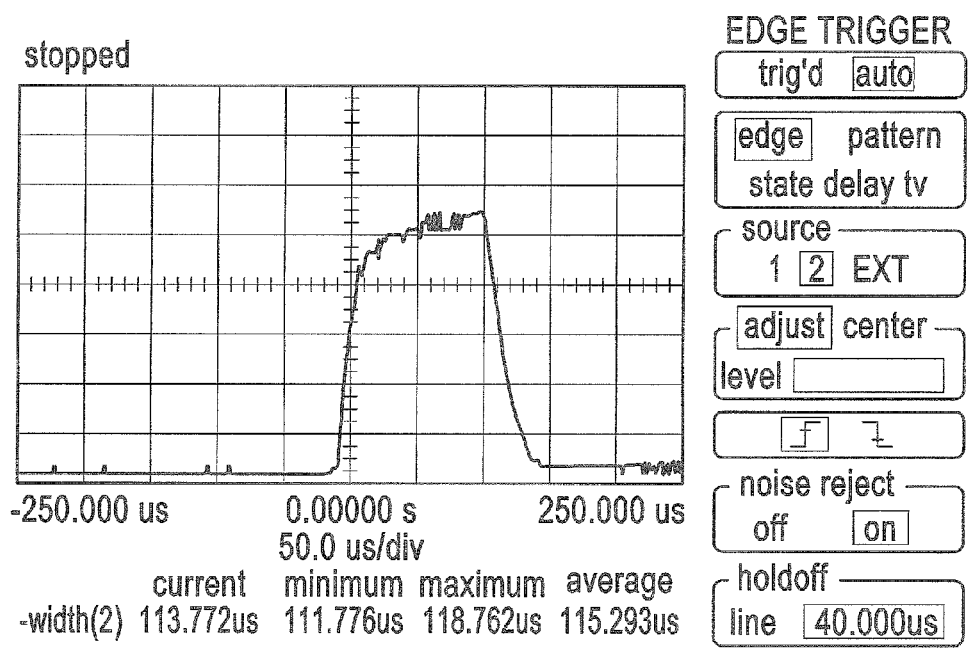
FIGS. 11A-C are photos of an oscilloscope readout illustrating flashlamp pulses produced by the IGBT system of FIG. 10.
Figure 11B:
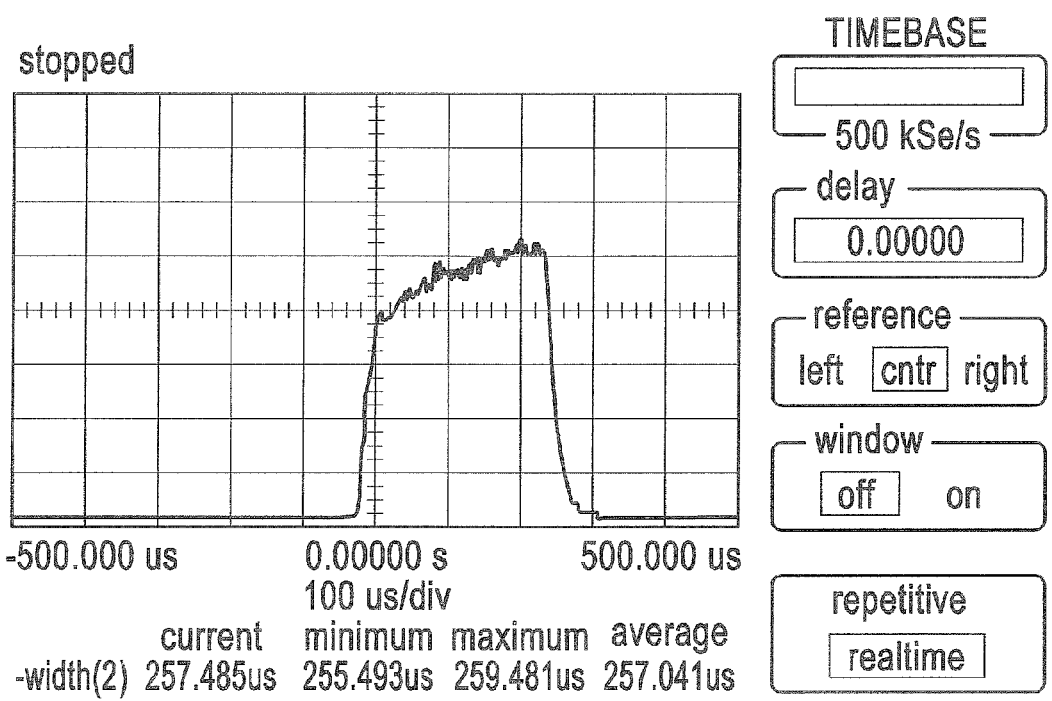
Figure 11C:
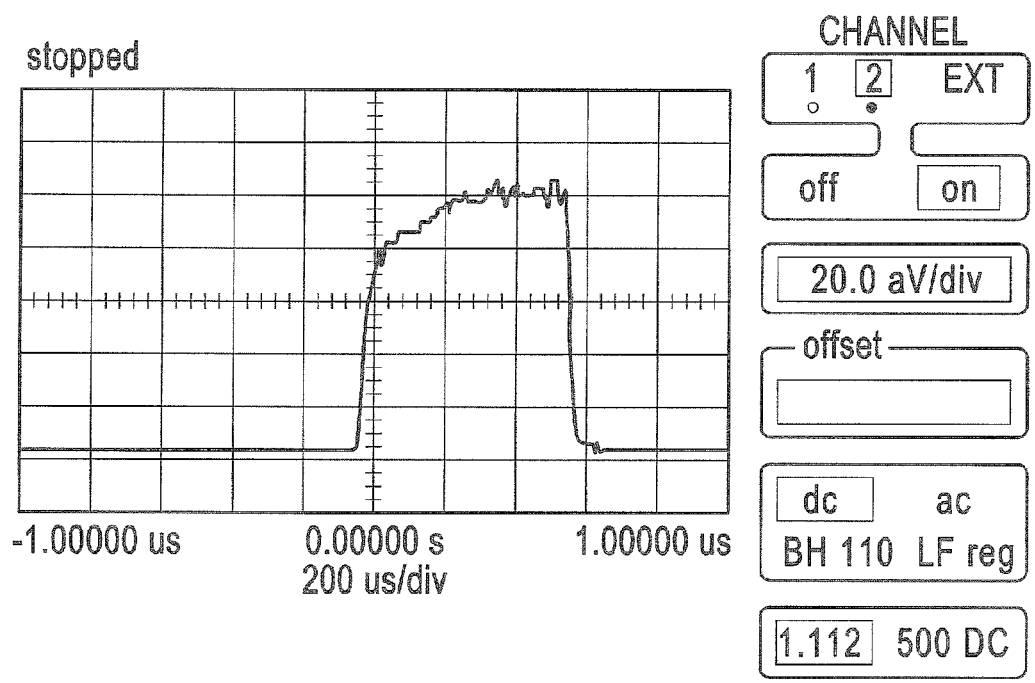

For endovenous laser treatment methods, typical values for the capacitor 844 and voltage 842 to control flashlamp pulses are:
C=1000 to 30,000 μFarads
V=100 to 500 volts These values can produce pulse lengths from 1 to 5000 μseconds, pump energies from 0.2 to 2000 joules per pulse, and laser output energies from 1 millijoules to 500 joules per pulse. FIGS. 11A-C are photos of oscilloscope readouts illustrating exemplary flashlamp pulses produced by the IGBT system of FIG. 10. For example, FIG. 11A illustrates a pulse length of about 110 μseconds, FIG. 11B illustrates a pulse length of about 250 μseconds, and FIG. 11C illustrates a pulse length of about 550 μseconds.

Those skilled in the art will recognize that there are other available methods to pulse lasers, but that the two methods described herein utilizing flashlamp pulse sources represent efficient and effective methods for producing high energy short pulses that are sufficient to vaporize blood coagulum formed at the tip of a fiber optic catheter in a blood vessel. Other laser pulse methods include the use of optical switches such as Pockels Cells or saturable dyes that bleach when intracavity energy densities exceed a calculated minimum. These methods produce very short pulses that can easily damage fiber optic delivery devices and are not preferred. It is also possible to mechanically shutter a continuous laser, but this would result in a very large and inefficient laser in which over 90% of the laser output would be wasted.

Figure 12:
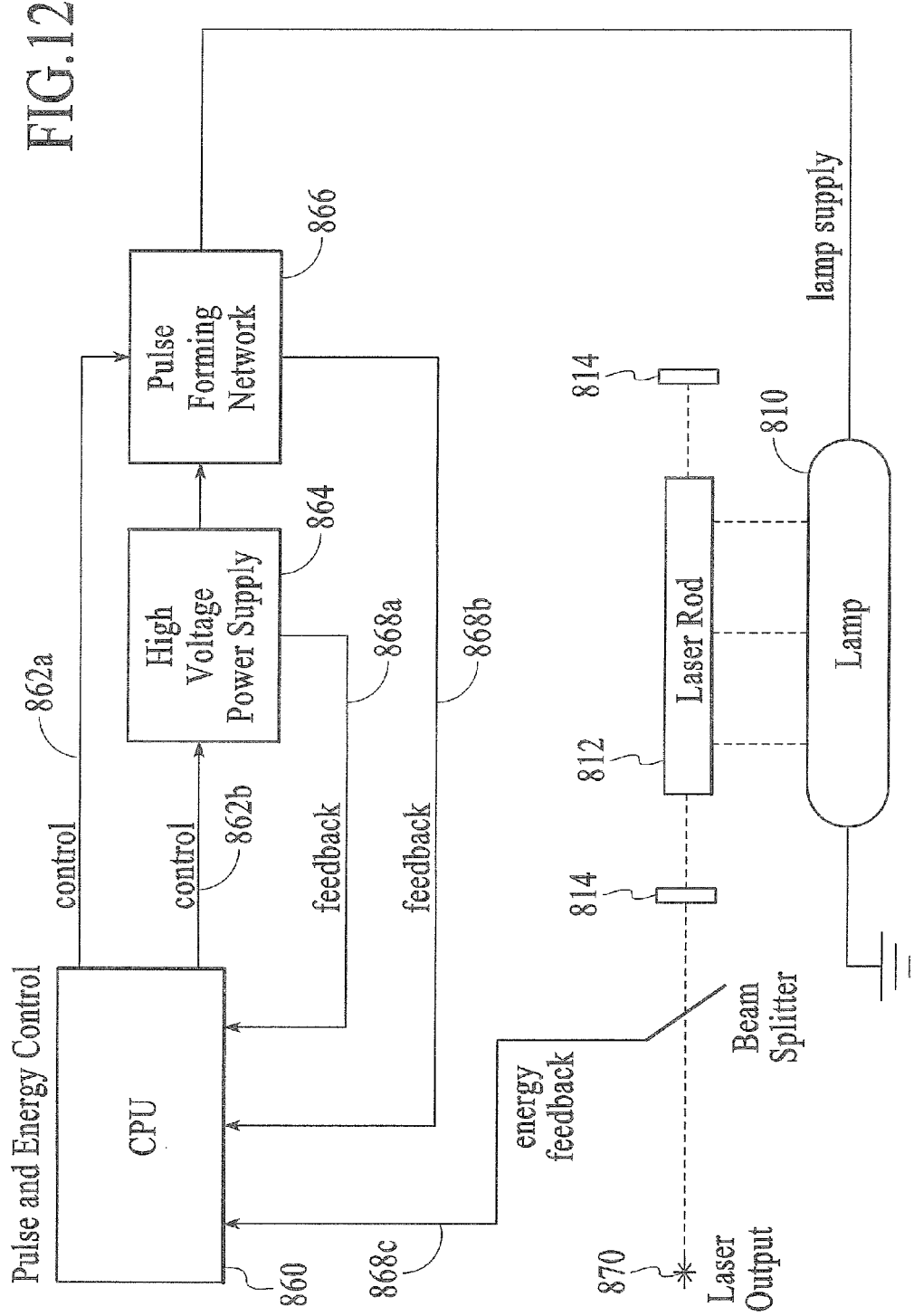
FIG. 12 is a schematic representation of a control system suitable for producing pulsed laser output.

FIG. 12 is a schematic representation of the controls needed to modify the pulse length and energy of a flashlamp pulsed laser. The energy and repetition rate of the pulsing is selected on a control panel attached to a central processing unit (CPU) 860. The CPU 860 sends control signals 862a-b to the high voltage power supply 864 and the pulse forming network 866 or electronic switch to select pulse energy and width. After each pulse, feedback signals 868a-c from the high voltage power supply 864, the pulse forming network 866, and the laser output 870 are routed back to the CPU 860 and compared for the correct energy and pulse. Energy and pulsing are thereby controlled on a real time basis.

EXPERIMENTAL RESULTS

Experiment #1

Coagulum Development with 1320 nm vs. 980 nm Laser

In a first experiment, coagulation formation on the fiber tip of an Nd:YAG pulsed laser having a wavelength of 1320 nm was compared to coagulation formation on the fiber tip of a Diode laser having a wavelength of 980 nm in continuous mode.

Method Overview:

Approximately 50 cc of porcine blood was stabilized with EDTA and placed in a beaker at room temperature. A standard 600 μm fiber was used on both laser systems. The power levels for both laser systems were measured using a Molectron PowerMax 600 power meter. The porcine blood was stirred between each interval. The fiber was cleaned using 3% hydrogen peroxide and wiped off with a Kim Wipe (®) between each firing. The fiber was checked using after each test to confirm a circular aiming beam with no tails, and checked by the power meter between each firing. Clot sizes were measured visually using a metric ruler and recorded in a lab notebook and digital photographs were taken.

Brief Results:

The 980 nm Diode laser operated in continuous mode created a large clot of coagulum on the fiber tip. The clot grew larger in size and hardened over the passage of time. The 1320 nm Nd:YAG laser operated in pulse mode did not create any significant coagulum clot until nearly 60 seconds of use, at which time a small clot was formed near the fiber tip.

Results:

|  | 980 Diode Laser | 1032 Nd:YAG Laser |
|---|---|---|
| Molectron (W) | Average Power = 5.72 watts, continuous mode | Average Power = 5.81 watts, @ 20 Hz/100 μsec pulse width |
|  | Peak Power = 5.72 watts | Peak Power = 2900 watts |
|  | Power Density = 2021 w/cm$^2$ | Power Density = 1,000,000 w/cm$^2$ |
| Time (seconds) |  |  |
| 5 | 1 mm × 2 mm clot, organized | No coagulum |
| 10 | 3 mm × 3 mm clot, organized | No coagulum |
| 15 | 3 mm × 4 mm clot, organized | No coagulum |
| 20 | 4 mm × 5 mm clot, organized | No coagulum |
| 25 | Not done | Not done |
| 30 | 3 mm × 6 mm clot, organized | No coagulum |
| 35 | Not done | No coagulum |
| 40 | Not done | No coagulum |
| 45 | 10 mm × 5-6 mm clot, organized | Possible ½ mm coating on tip |
| 50 | Not done | Possible ½ mm coating on tip |
| 60 | 8 mm × 6 mm, organized hard clot | 1 mm × 2 mm clot, soft |

Conclusions:

The results demonstrated a marked difference in clot formation between the 1320 Nd:YAG pulsed laser and the 980 Diode laser in continuous mode. Clot formation with the 980 Diode occurs within the first 5 seconds of use. The 1320 Nd:YAG pulsed laser does not produce a definable clot until 60 seconds of continuous firing. Other experiments, described below, have shown that the repetition rate of 20 Hz will "self-clean" the tip by pulsing the clot off the fiber tip.

Experiment #2

Coagulum as a Function of Laser Power and Power Density

In a second experiment, coagulation formation on a fiber tip was measured as a function of laser peak power and power density for an Nd:YAG laser having a wavelength of 1320 μm.

Method Overview

Approximately 10 cc of porcine blood was stabilized with EDTA and placed in a graduated cylinder at room temperature. A standard 600 μm fiber and a 365 μm fiber were each used to deliver energy to the blood medium. Clot sizes were measured using a metric ruler.

First Test:

The first test was to compare coagulation accumulations between the 600 μm fiber and the 365 μm fiber.

| System | Settings | | Time | Fiber | Power Density | Aiming Beam |
|---|---|---|---|---|---|---|
| 1320 nm | 7 W/50 Hz | 140 mJ/pulse @ width = 150 μsec | 5-40 sec | 600 μm | 330,000 W/cm$^2$ | None thru clot |
| 1320 nm | 7 W/50 Hz | 140 mJ/pulse @ width = 150 μsec | 5-40 sec | 365 μm | 1,000,000 W/cm$^2$ | None thru clot |

Clot formation was compared at 5-second intervals for both fibers. Coagulum was cleaned off with a Kim Wipe (®) between each firing. The aiming beam was observed after each run. If the aiming beam was found not to be circular, the fiber was replaced.

| Time(seconds) | 365 μm | 600 μm |
|---|---|---|
| 5 | No coagulum | No coagulum |
| 10 | No coagulum | No coagulum |
| 15 | No coagulum | No coagulum |
| 20 | No coagulum | ~2-3 mm, soft clot |
| 25 | No coagulum | ~2-3 mm, soft clot |

-continued

| Time(seconds) | 365 μm | 600 μm |
|---|---|---|
| 30 | ~1-2 mm, very soft clot | ~3-4 mm, soft |
| 35 | ~2-3 mm, somewhat harder | ~4-5 mm clot |
| 40 | ~3-4 mm clot, organized | ~5-6 mm clot |

Both fibers provided circular aiming beams having no tails after each test.

The results suggest that clot formation is less with higher power density.

Second Test:

Compare coagulum formation with energy density using 600 μm fiber.

| System | Settings | | Time | Energy Density | Coagulum | Aiming Beam |
|---|---|---|---|---|---|---|
| 1320 nm | 7 W/50 Hz | 140 mJ/pulse @ width = 150 μsec | 90 sec | 50 J/cm2 | 8-10 mm, eccentric soft clot | None thru clot |
| 1320 nm | 7 W/50 Hz | 350 mJ/pulse @ width = 440 μsec | 90 sec | 124 J/cm2 | 5-6 mm, soft clot | Visible beam thru clot |

The results suggest higher energy per pulse produces less coagulum and a fiber tip that is kept "cleaner" as demonstrated by the aiming beam being visible after the test.

Third Test:

Determine the capability of a high energy density laser operation to prevent clot formation over the laser emitting end of the fiber.

Method Overview:

Approximately 40 cc of porcine blood (EDTA stabilized) was placed in a 100 cc beaker. A separate beaker was used for each system tested. Separate fibers were used for each system tested. After each firing, fibers were cleaned by immersing in a 3% hydrogen peroxide solution and wiping dry with a Kim Wipe (®), after which the aiming beam was checked for circularity and the power was checked with the Molectron PowerMax 600 power meter. Power variations from firing to firing were kept to between +/−3%. In addition, prior to firing, each beaker of porcine blood was stirred to evenly distribute the serum and red blood cells.

| System | Settings | Energy Density | Time | Fiber Type | | Coagulum | Aiming Beam |
|---|---|---|---|---|---|---|---|
| 1320 nm | 5.31 Watts 106 mJ/pulse | 37 Joules/cm² | 20 sec | 600 μm | | | |
| | | | | | Run #1 | 3 mm clot, organized, semi soft | None |
| | | | | | Run #2 | 4 mm clot, organized, semi soft | None |
| | | | | | Run #3 | 5 mm clot, organized, semi soft | None |
| 1320 nm | 5.40 Watts 270 mJ/pulse | 95 Joules/cm² | 20 sec | 600 μm | | | |
| | | | | | Run #1 | ½ mm clot, organized | Yes, good |
| | | | | | Run #2 | 2 mm clot, organized | Round beam |
| | | | | | Run #3 | 1 mm clot, organized | Good, slightly fuzzy |

Results:

More energy per pulse aids in reducing clot volume and maintaining energy output from the fiber tip as demonstrated by the aiming beam being observed in the higher energy density runs.

Fourth Test:

A fourth test was conducted to determine whether changing to a higher energy density will disrupt or cause removal of a clot that has formed on a fiber tip.

Method Overview:

A clot was formed on a 600 μm fiber using a 1320 nm laser @ 6 Watts/50 Hz (measured energy 5.56 Watts). The clot size was measured and its structure recorded. The fiber was then re-inserted into the porcine blood test beaker. The laser was adjusted to higher energy densities as in the table below.

| | Time-Additive | Result: |
|---|---|---|
| Energy Density: 169 Joules/cm$^2$ | 10 sec | Clot increased in size, ~5 × 10 mm, no aiming beam visible |
| Clot Description #1: ~4 × 8 mm, organized, no aiming beam | 15 sec | Clot perforated, aiming beam is visible |
| | 15 sec | No additional clot formation, aiming beam visible |

| | Time-Additive | Result: |
|---|---|---|
| Energy Density: 98 Joules/cm$^2$ | 10 sec | No change in size, no aiming beam visible |
| Clot Description #2: ~5 × 10 mm, organized, no aiming beam | 15 sec | Hole produced in clot distal end, aiming beam now present |
| | 15 sec | No additional increase in size, aiming beam present |

Conclusions:

Energy densities of 98 and 169 Joules/cm2 at the fiber tip will maintain an energy pathway from the fiber tip by ablating off accumulated blood coagulum.

Figure 13A:
FIG. 13A is a schematic representation of a clean tip of an optical fiber.
Figure 13B:
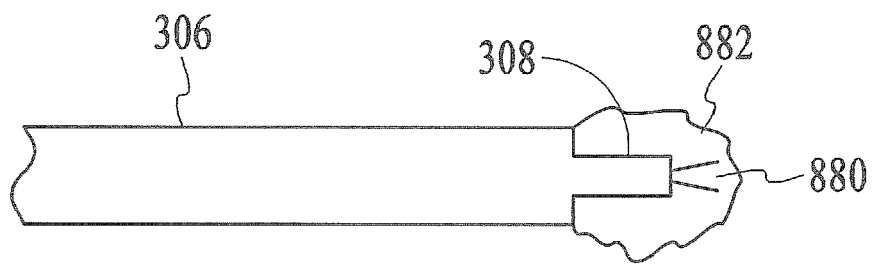
FIG. 13B is a schematic representation of an optical fiber having coagulum formed thereon.
Figure 13C:
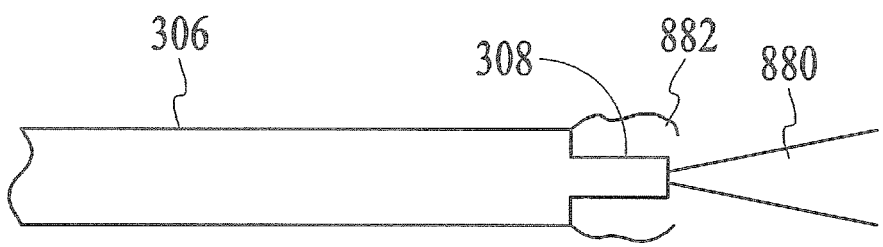
FIG. 13C is a schematic representation of an optical fiber having coagulum formed thereon after pulsed laser exposure.

These results are illustrated in FIGS. 13A-C. Turning first to FIG. 13A, an optical fiber 306 is shown having a clean fiber tip 308. The aiming beam 880 is unobstructed and is easily visible. Next, in FIG. 13B, a clot 882 is formed on the fiber tip 308. The clot 882 effectively blocks the aiming beam 880, which is no longer visible. Finally, in FIG. 13C, laser energy having sufficient energy density to ablate off the accumulated coagulum is passed through the fiber tip 308. The laser energy effectively self-cleans the fiber optic tip 308, making the aiming beam 880 visible again.

Experiment #3

Endovenous Ablation with Laser Induced Thrombolysis

Thermally induced thrombus is common during treatment of varicose veins with laser or radiofrequency catheters, and can potentially reduce procedure efficiency and cause vein wall perforations. Proximal thrombus can break off into the venous system and intravenous thrombus can mask non-closed segments. To determine the requirements for minimal thrombus formation, various pulsed and continuous wave lasers and various fibers were fired in a 15 ml sample of porcine blood. The resulting coagulum was measured. All continuous wave lasers generated coagulum on the fiber tip, regardless of wavelength or fiber design. Pulsed wave lasers did not generate as much coagulum on the fiber tip. Protected or encapsulated tip fibers did not eliminate coagulum formation, although fiber cladding design appears to affect coagulum formation. Coagulum formation may be minimized by electing a 1320 nm pulsed laser with a short pulse length, higher energy per pulse, and a fiber of smaller diameter.

Experimental Setup

Equipment Used

Various lasers with differing settings were utilized during this experiment. Continuous wave diode lasers of wavelengths 810 nm, 940 nm, 980 nm, 1310 nm and 1470 nm were used as well as a pulsed 1320 nm Nd:YAG laser with rep rates 20 and 50 Hz, pulse lengths 100, 300, 500, and 1000 μsec; a pulsed 1064 nm Nd:YAG laser with rep rates 20 and 50 Hz and pulse length 100 μsec; a pulsed 2100 nm THC:YAG laser with rep rate 10 Hz and pulse length 350 μsec; and a pulsed 1320 nm CoolTouch® CTEV® laser with rep rate 50 Hz and pulse length 150 μsec. All lasers were calibrated to operate at 7 watts. Fibers of varying specifications were used: 550 μm core Silica Clad (all silica) NA=0.21 low OH; 550 μm core Hard Plastic Clad NA=0.37 low OH; 365 μm core Silica Clad NA=0.21 low OH; protected tip (metal sleeve); and encapsulated tip (quartz capillary).

Experimental Methods

For 10 trials the laser was fired in 15 mL of porcine blood in Sodium EDTA in a 10 mL graduated cylinder for 30 seconds while being pulled back at 0.5 mm/sec. The fiber was introduced to the same depth for each trial. The temperature was taken after each trial at the same depth. The starting room and blood temperature were also recorded. After each trial, the cap-tipped fibers were wiped clean of coagulum with a pre-tared KimWipe, which was then weighed a second time to determine the mass of the coagulum formed. While testing the encapsulated or protected fibers, the power of the laser was recorded between trials. The other fibers were clipped and the resulting fiber piece was weighed with the coagulum still attached. This fiber piece was then cleaned and weighed, and its mass was subtracted from the mass of fiber and attached coagulum to obtain the mass of only the coagulum. The fiber was then stripped and cleaved to produce a clean tip for the next trial. The porcine blood in the graduated cylinder was stirred and inverted several times between each trial. Each 15 mL sample of blood was used for no more than 10 trials, after which the blood was saved for possible further analysis. Two bags of porcine blood were used. Depending on the bag of blood being used, the data was designated as series 1 or series 2 for analysis and comparison. Series 2 blood coagulated less than series 1.

Results

Figure 14:
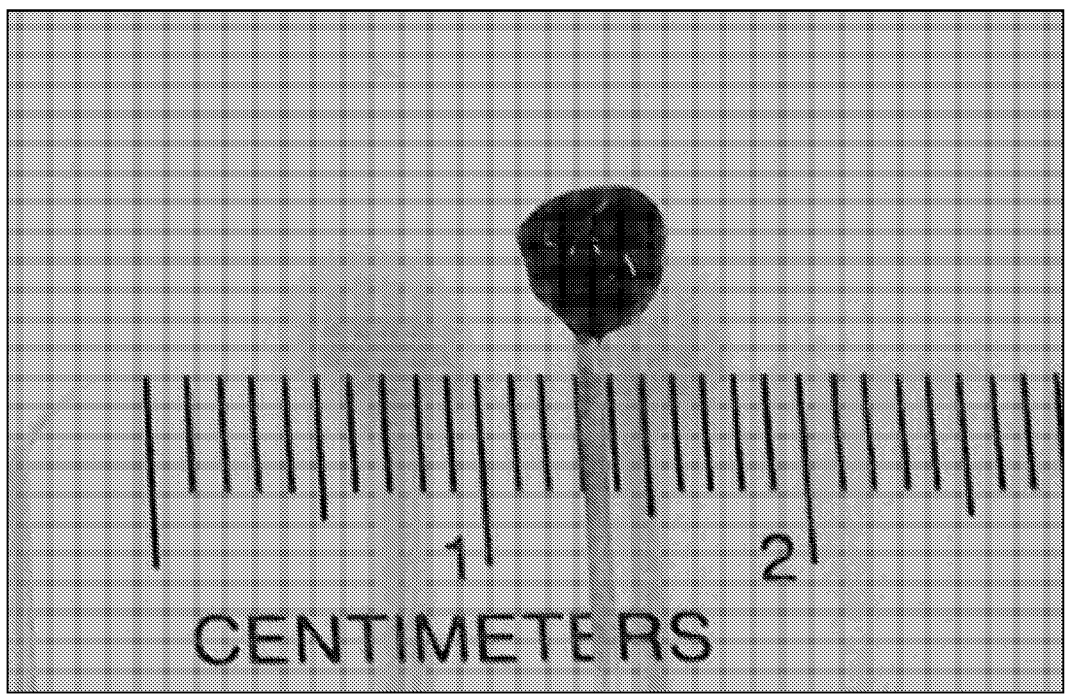
FIG. 14 is a photograph of experimentally obtained porcine blood coagulum formed using 980 nm CW laser.
Figure 15:
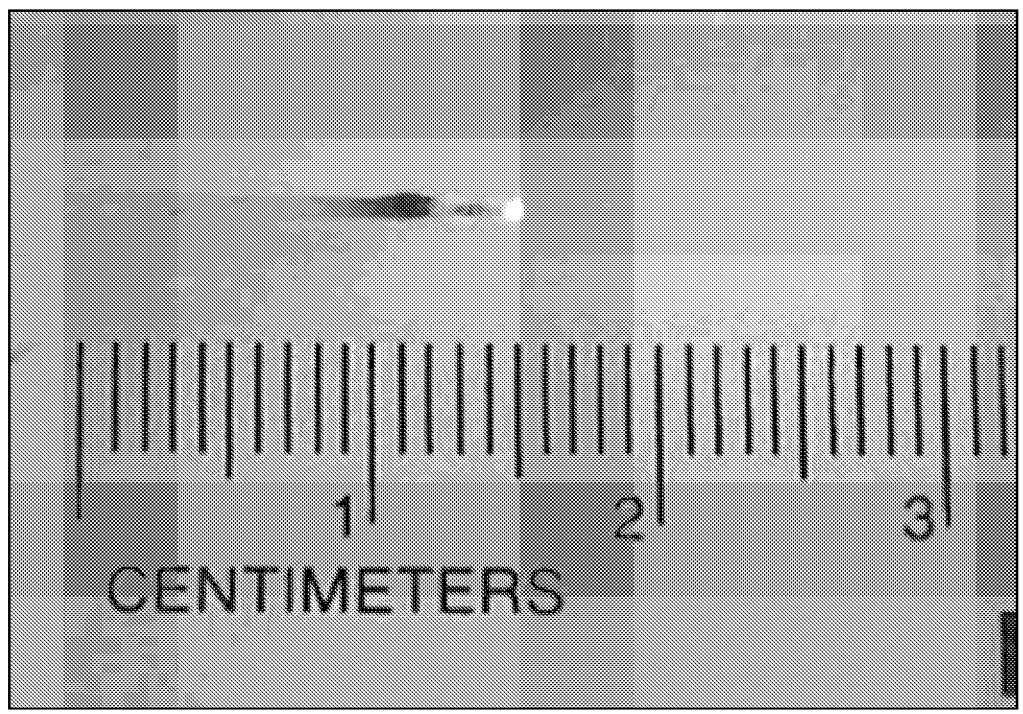
FIG. 15 is a photograph of experimentally obtained porcine blood coagulum formed using 1320 nm pulsed wave laser.

FIG. 14 is a photograph of experimentally obtained porcine blood coagulum formed using 980 nm CW laser. FIG. 15 is a photograph of experimentally obtained porcine blood coagulum formed using 1320 nm pulsed wave laser.

According to the experimental data, continuous wave lasers did not generate as much coagulum as pulsed wave lasers. As is shown in FIG. 14, the coagulum formed with a continuous wave laser is visually noticeable, while, as in FIG. 15, the coagulum from a pulsed wave laser submitted to the same experimental conditions is nearly non-existent.

Figure 16:
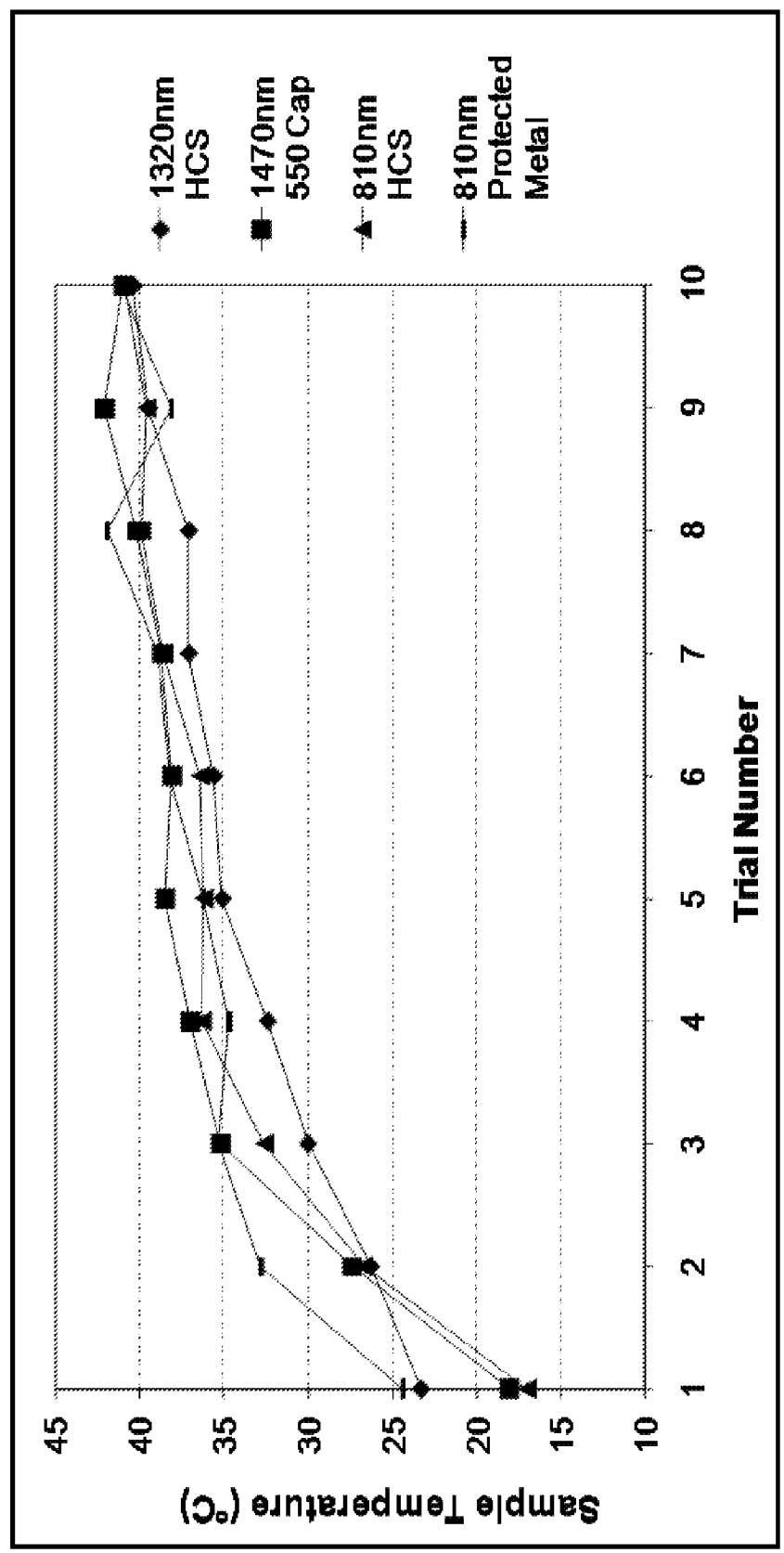
FIG. 16 is a graph of experimentally obtained temperature of blood sample as related to the number of trials conducted in the blood sample.

FIG. 16 is a graph of experimentally obtained temperature of blood sample as related to the number of trials conducted in the blood sample. The temperature of the blood sample through which the fiber was drawn back was monitored at certain intervals. Sample temperature rose at a similar rate for every fiber/laser combination tested, as best shown in FIG. 16.

Figure 17:
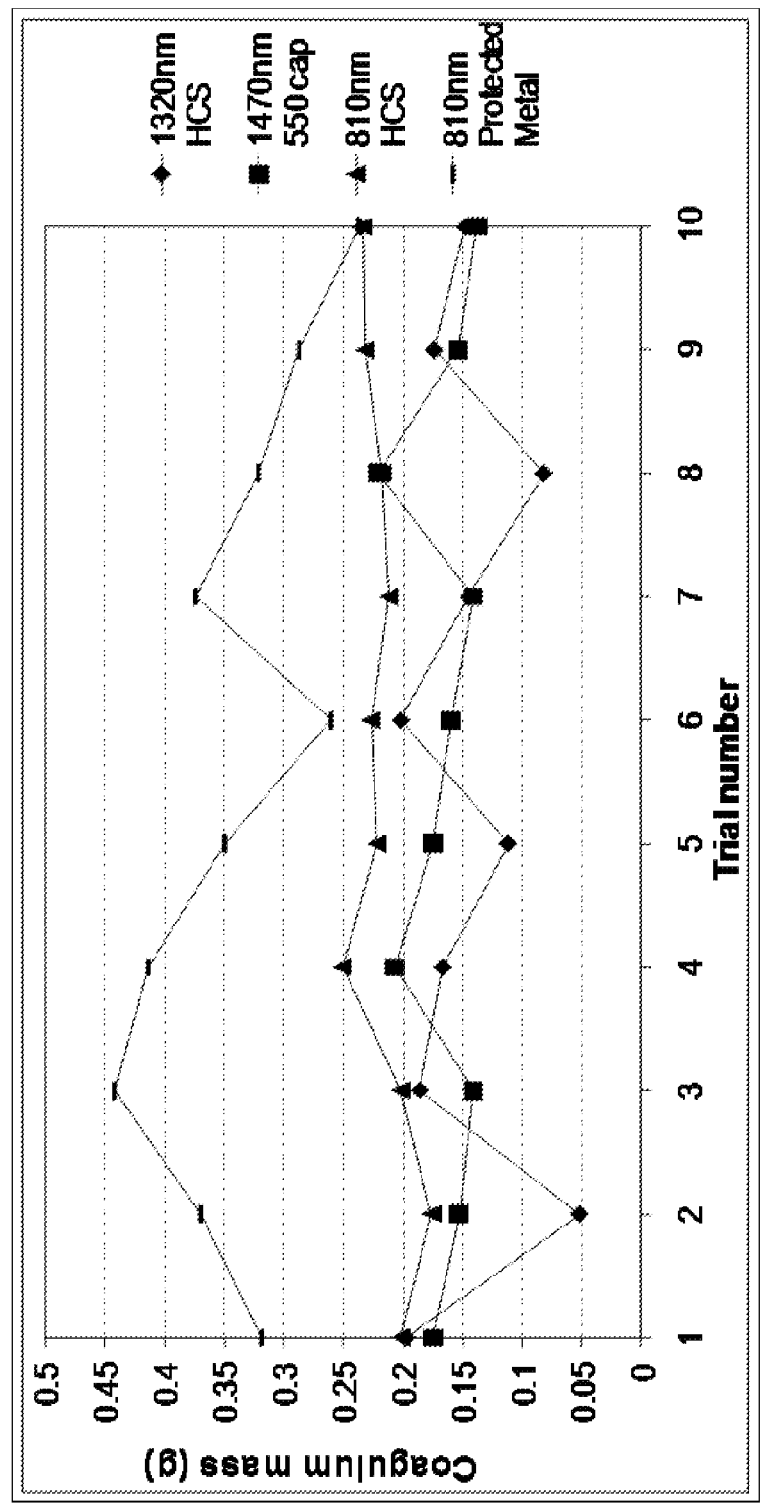
FIG. 17 is a graph of experimentally obtained weight of porcine blood coagulum formed on fiber tip as related to the number of trials already conducted in the blood sample.

FIG. 17 is a graph of experimentally obtained weight of porcine blood coagulum formed on fiber tip as related to the number of trials already conducted in the blood sample. The number of trials already conducted within a certain blood sample was not found to influence the weight of the coagulum formed. Therefore, while the temperature rose with the number of trials, coagulum weight was not significantly influenced by sample temperature (FIG. 17).

Figure 6:
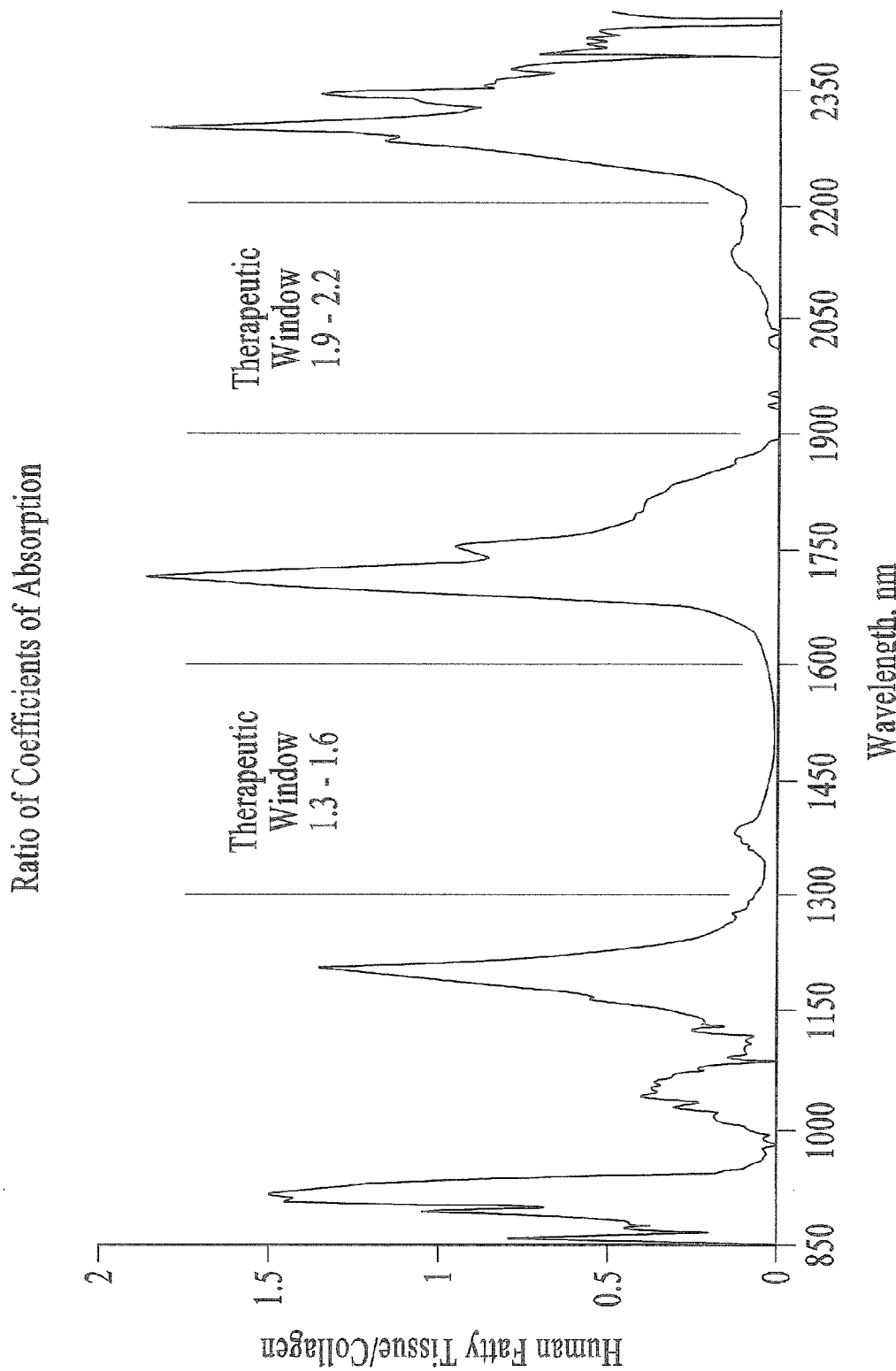
FIG. 6 is a graphical illustration showing curves for the ratio of the absorption coefficients of human fatty tissue and collagen as a function of energy wavelength.
Figure 18:
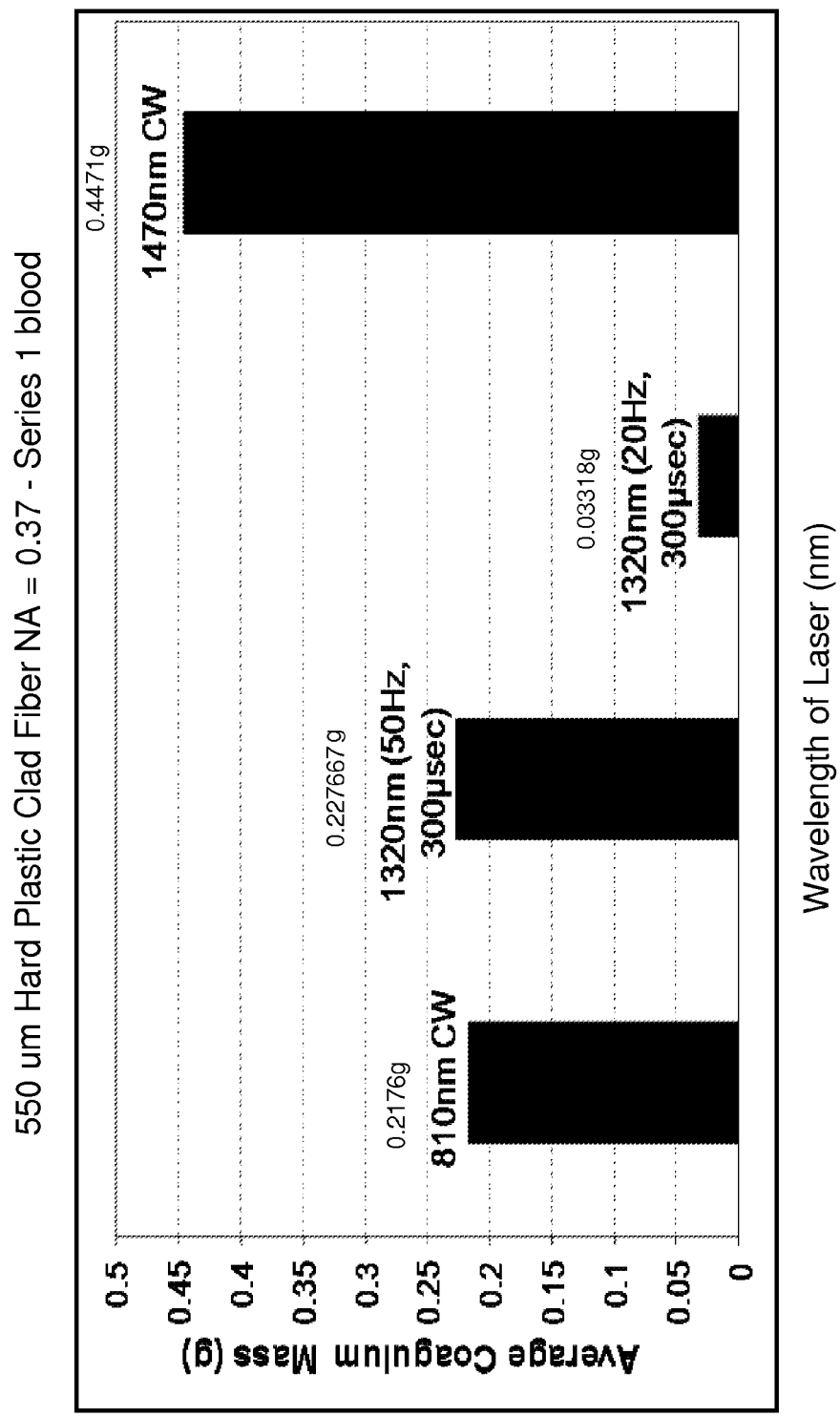
FIG. 18 is a plot of experimentally obtained average mass of porcine blood coagulum formed using a 550 μm Hard Plastic Clad fiber NA=0.37.
Figure 19:
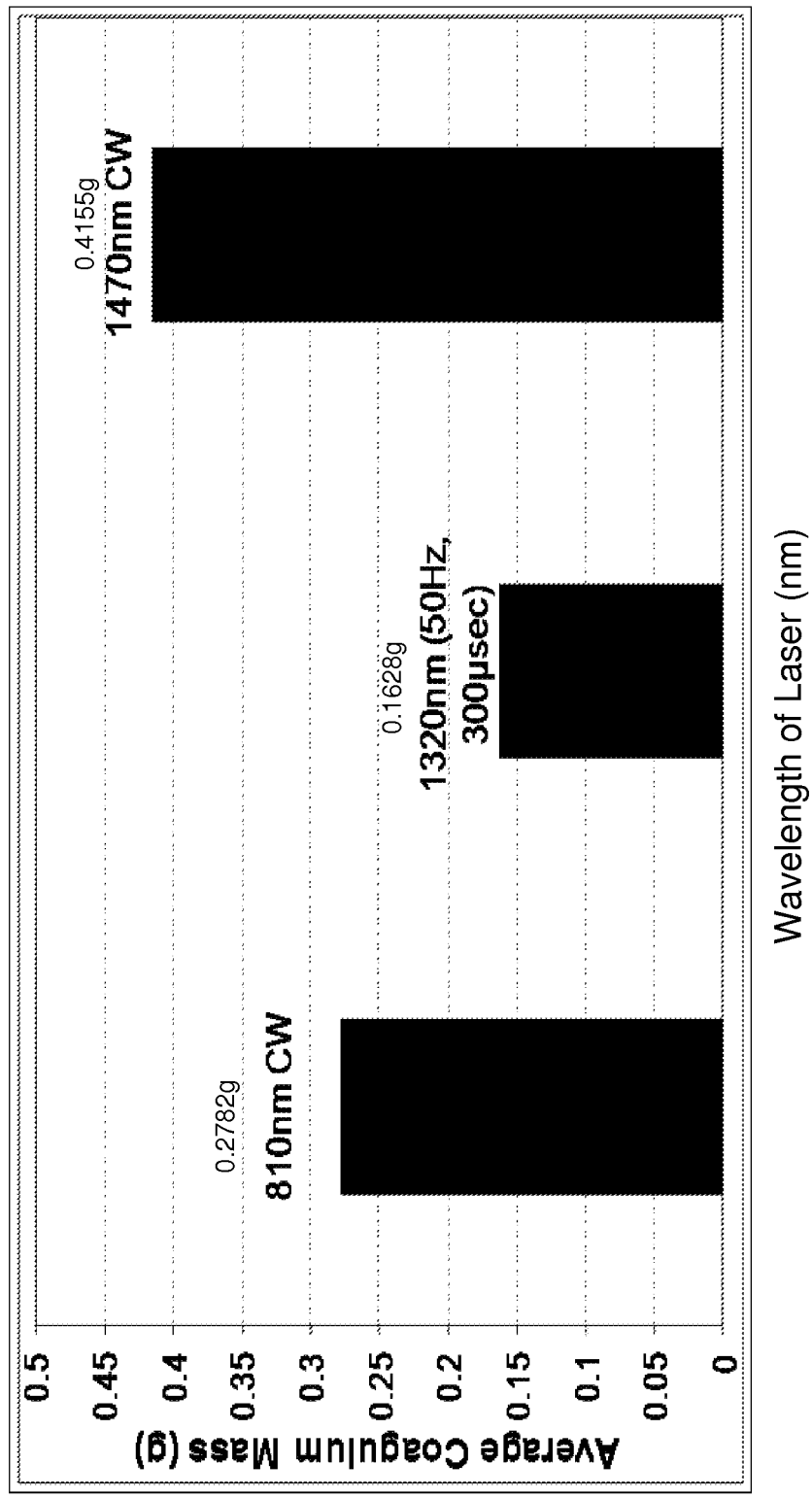
FIG. 19 is a plot of experimentally obtained average mass of porcine blood coagulum formed using a 550 μm All Silica fiber NA=0.21.

FIG. 18 is a plot of experimentally obtained average mass of porcine blood coagulum formed using a 550 μm Hard Plastic Clad fiber NA=0.37. FIG. 6 is a plot of experimentally obtained average mass of porcine blood coagulum formed using a 550 μm All Silica fiber NA=0.21. Series 1 blood and 7 watts power was used for all trials. FIG. 19 is a plot of experimentally obtained average mass of porcine blood coagulum formed using a 550 μm All Silica fiber NA=0.21.

With every fiber type, continuous wave (CW) diode lasers generated more coagulum on the fiber tip than pulsed lasers, regardless of the wavelength. This trend is apparent in FIGS. 18 and 19.

Figure 20:
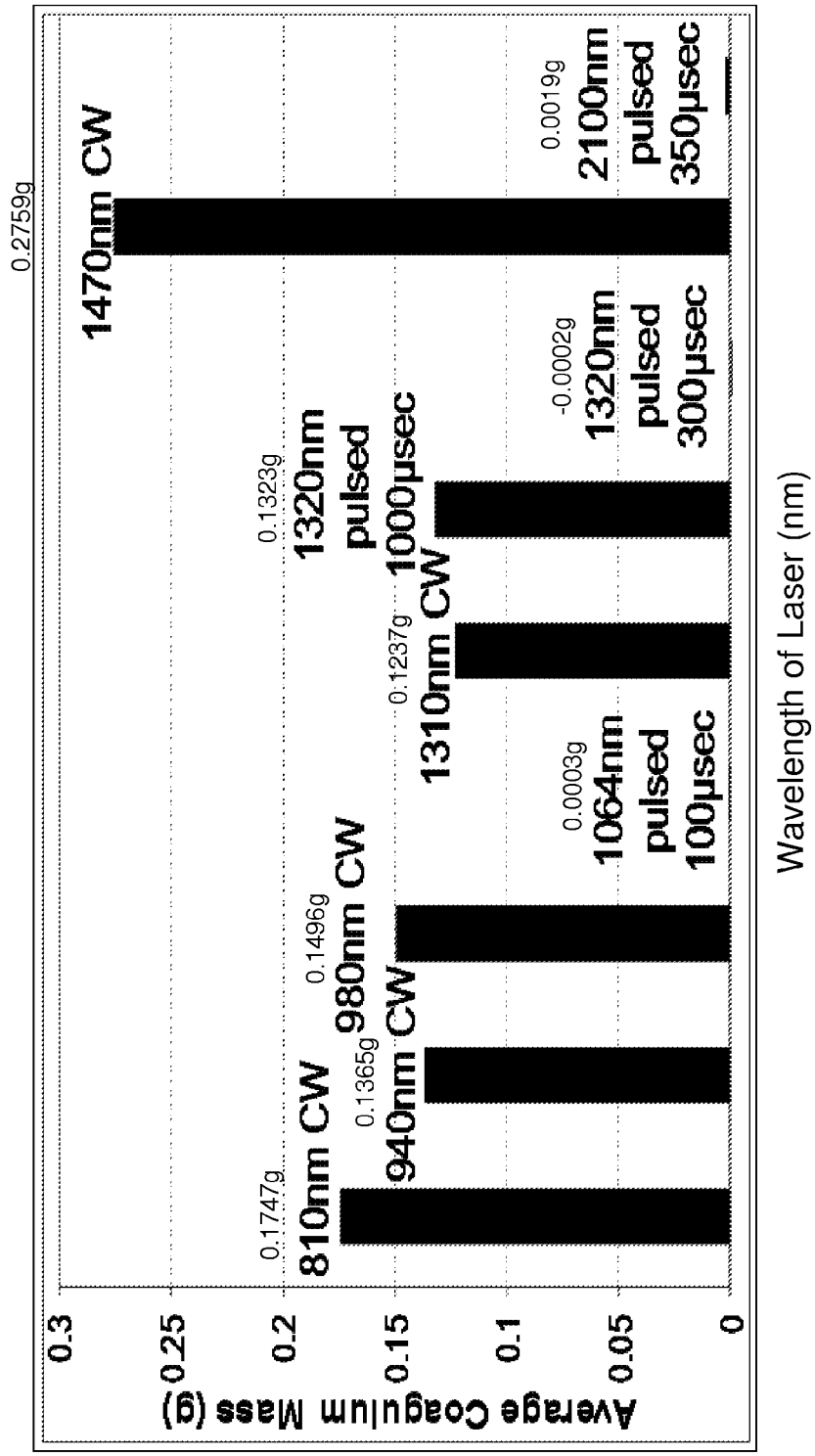
FIG. 20 is a plot of experimentally obtained average mass of porcine blood coagulum formed using a 550 μm All Silica fiber NA=0.21.

FIG. 20 is a plot of experimentally obtained average mass of porcine blood coagulum formed using a 550 μm All Silica fiber NA=0.21. Series 2 blood and 7 watts power were used for all trials. FIG. 8 is a plot of experimentally obtained average mass of porcine blood coagulum formed using a 365 μm All Silica fiber NA=0.21. Series 1 blood and 7 watts power were used for all trials. FIG. 9 is a plot of experimentally obtained average mass of porcine blood coagulum formed using a 365 μm All Silica fiber NA=0.21. Series 2 blood and 7 watts power were used for all trials.

Figure 21:
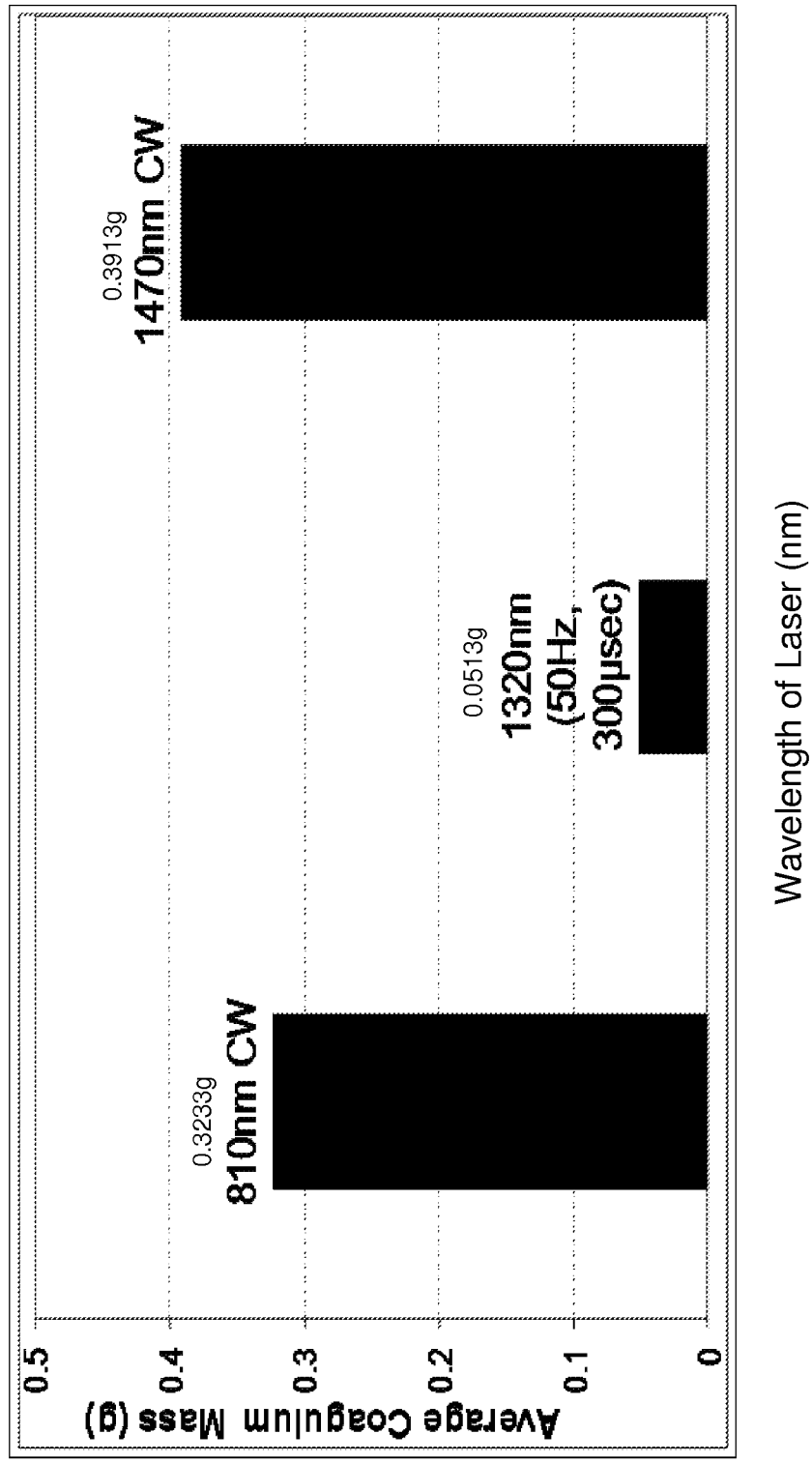
FIG. 21 is a plot of experimentally obtained average mass of porcine blood coagulum formed using a 365 μm All Silica fiber NA=0.21.
Figure 22:
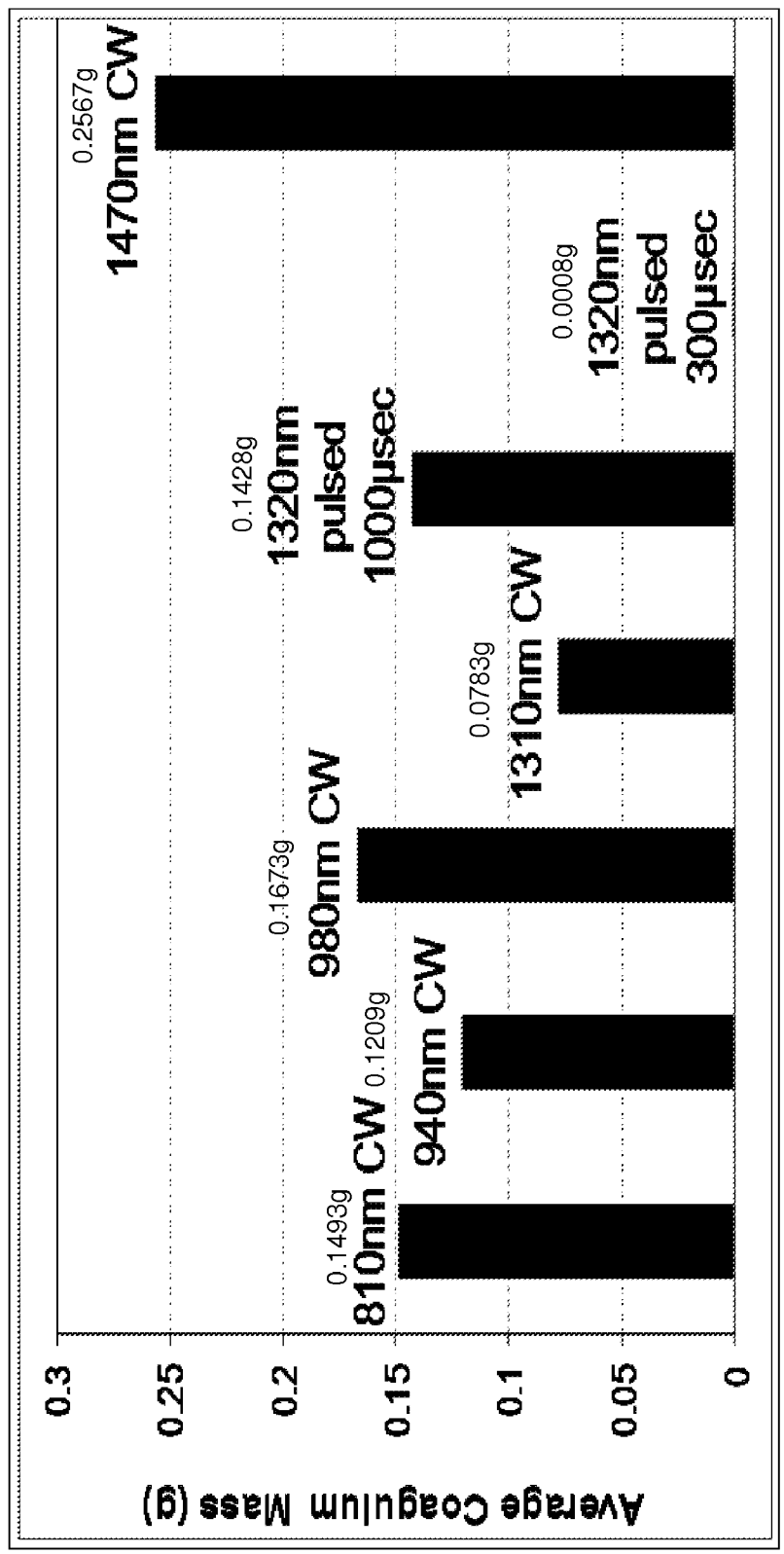
FIG. 22 is a plot of experimentally obtained average mass of porcine blood coagulum formed using a 365 μm All Silica fiber NA=0.21.

Although the series 2 blood formed different amounts of coagulum than the series 1 blood, the same trend of coagulation mass was clearly visible with relation to laser specifications. With the exception of the 1320 nm laser operating at 1000 μsec pulse length, all of the pulsed lasers failed to form a significant amount of coagulum as best shown in FIG. 20. Under the same parameters, the pulsed 1320 nm laser produced less coagulum when used with the 365 μm all silica fiber as best shown in FIG. 21 than with the 550 μm all silica fiber as best shown in FIG. 19. In fact, lasers of almost every wavelength generated less coagulum when used with a 365 μm all silica fiber as best shown in FIG. 22 instead of a 550 μm all silica fiber as best shown in FIG. 20.

Figure 23:
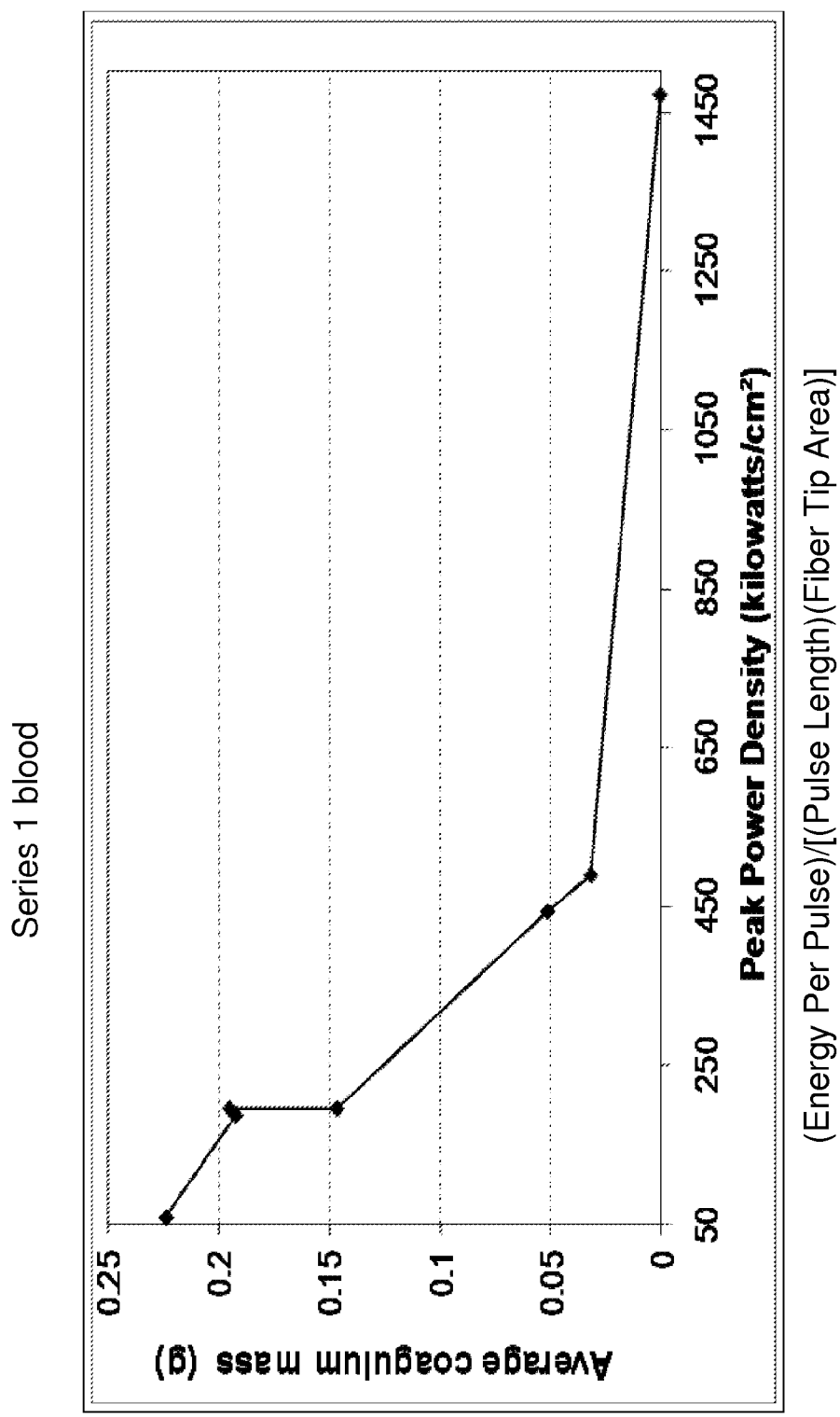
FIG. 23 is a plot of experimentally obtained average mass of porcine blood coagulum as related to peak power density.
Figure 24:
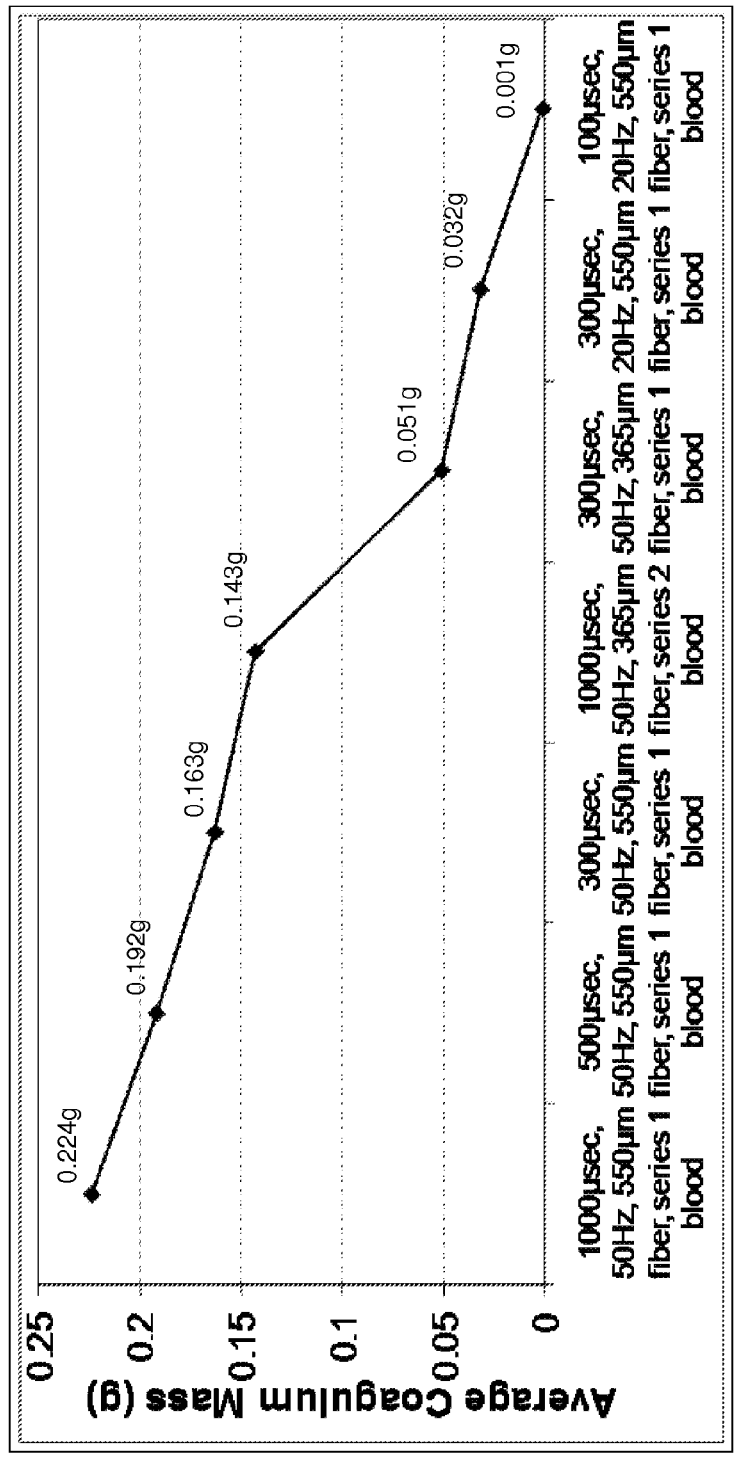
FIG. 24 is a plot of experimentally obtained average mass of porcine blood coagulum formed using differing fibers and pulse lengths with a pulsed 1320 nm laser.
Figure 25:
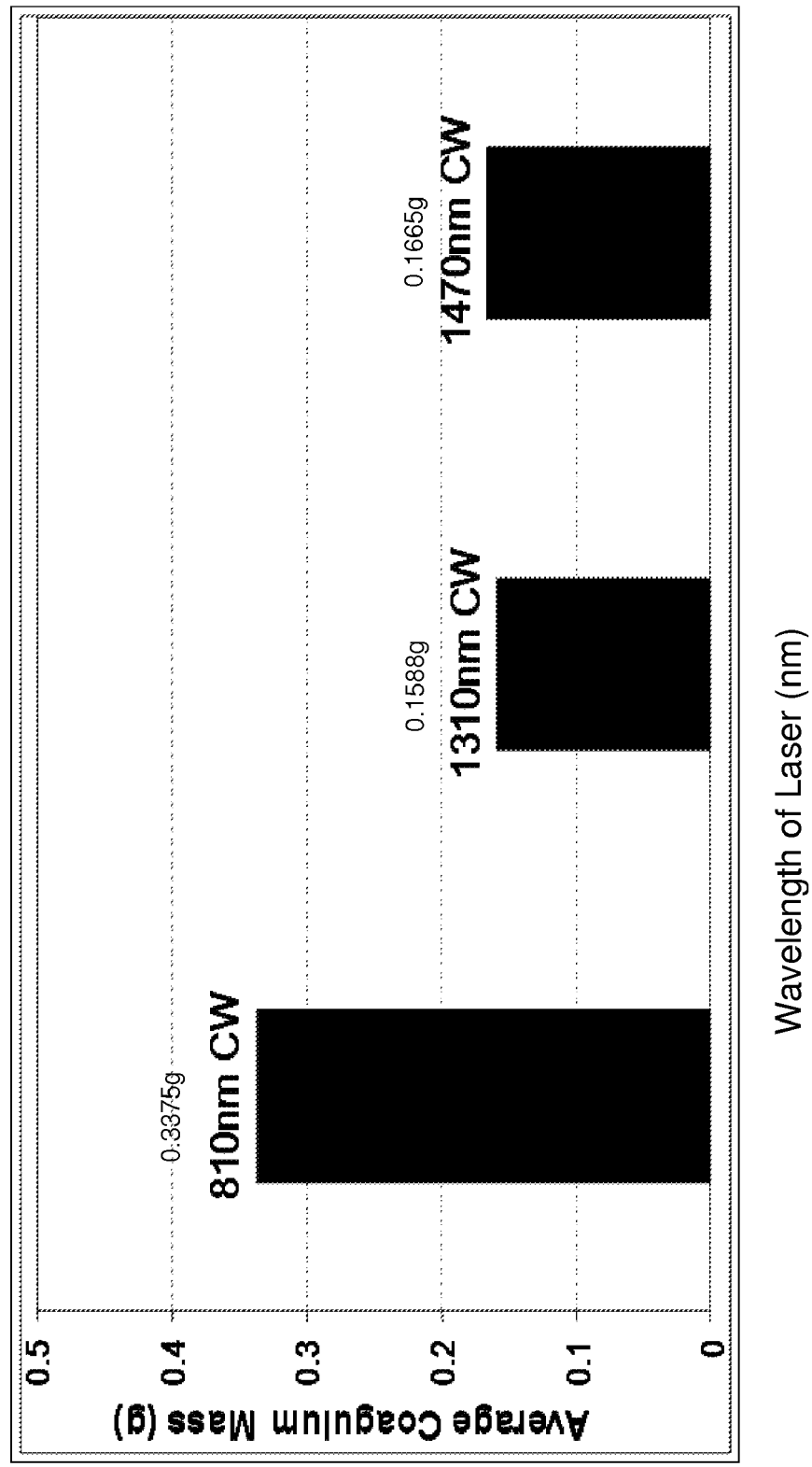
FIG. 25 is a plot of experimentally obtained average mass of porcine blood coagulum formed using a protected tip fiber.
Figure 26:
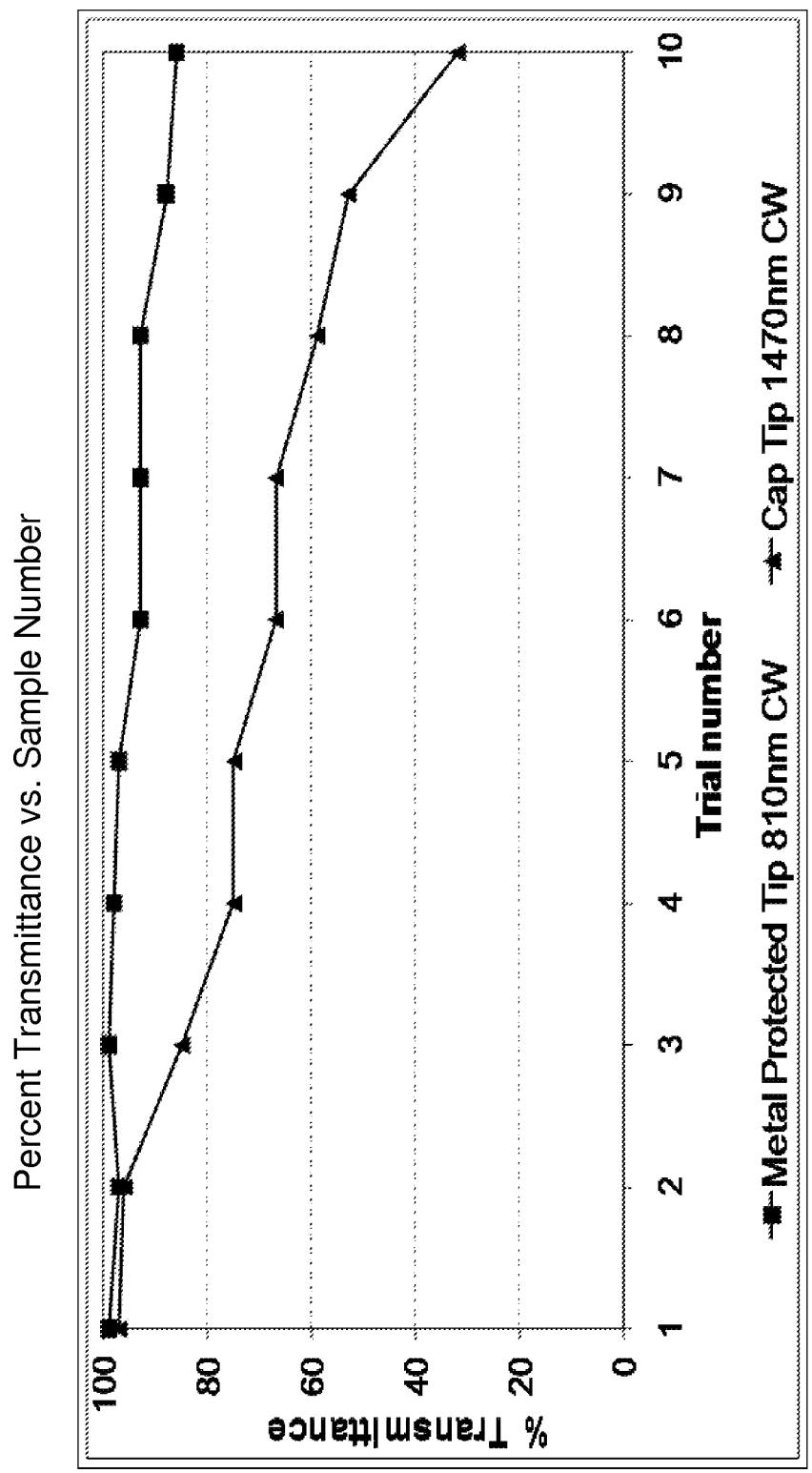
FIG. 26 is a plot of experimentally obtained percent transmittance of protected and cap tip fibers after each trial.

FIG. 23 is a plot of experimentally obtained average mass of porcine blood coagulum as related to peak power density. Series 1 blood was used for all trials. FIG. 24 is a plot of experimentally obtained average mass of porcine blood coagulum formed using differing fibers and pulse lengths with a pulsed 1320 nm laser. All trials were conducted at 7 watts power. FIG. 25 is a plot of experimentally obtained average mass of porcine blood coagulum formed using a protected tip fiber. Series 1 blood was used for all trials. FIG. 26 is a plot of experimentally obtained percent transmittance of protected and cap tip fibers after each trial.

The peak power density of the pulsed laser/fiber combination was found to be inversely proportional to the average amount of coagulation that said combination would generate as shown in FIG. 23. Pulsed lasers with kilowatt peak powers did not generate coagulum on the fiber tip. FIG. 24 shows in descending order the combinations of pulse length, rep rate, and fiber diameter that produced the most coagulum, including a table of the treatment parameters and obersevations. Protected tip or encapsulated tip fibers did not eliminate coagulum formation as shown in FIG. 25 and were found to lose transmittance the more times they were used as shown in FIG. 26.

Conclusions

Coagulum formation is affected by laser wavelength used, pulse length, energy per pulse, diameter of fiber used, and the fiber cladding design. Coagulum formation may be minimized by using a pulsed laser with a shorter pulse length between 150-300 μsec, a rate of repetition of 20-50 Hz, and 365-550 μm diameter fibers.

Experiment #4

A Comparison of Laser Delivery Mode & Wavelength on Varicose Veins

Purpose:

To determine the effects of endovenous laser wavelengths and delivery modes (continuous diode versus pulsed Nd:YAG) on isolated veins ex-vivo both macroscopically as well as microscopically. In addition, to determine whether protected-tip fibers are effective in reducing vein wall perforations.

Methods:

An ex-vivo endovenous laser ablation model was used. Human veins harvested during ambulatory phlebectomy procedures were sutured closed at one end. Portions of vein were then suspended by adding a weighting device, within a graduated column of warm saline at physiologic concentration. The lumen of each vein was filled with porcine blood, a fiber inserted into the lumen and the fiber attached to a mechanical pullback device.

Figures 27A, 27B:
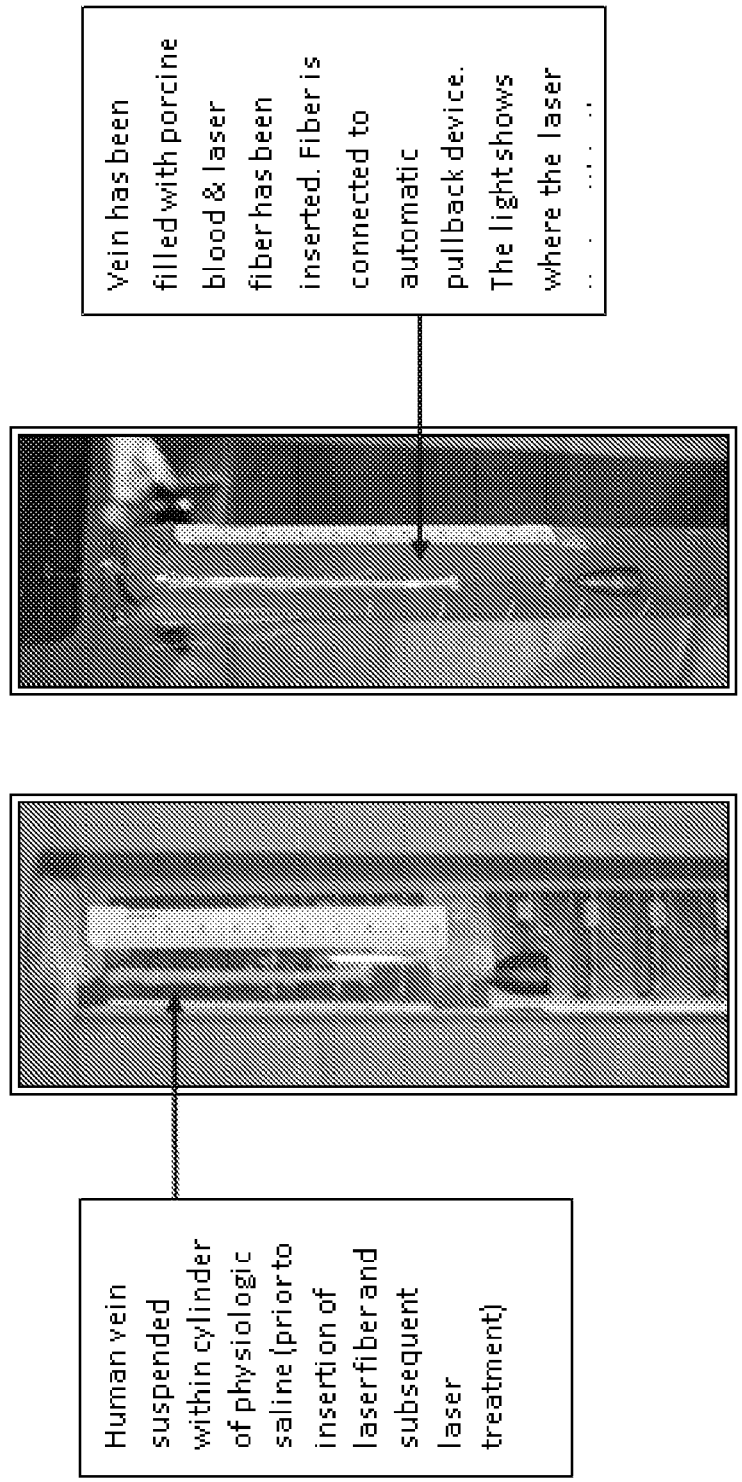
FIG. 27A shows a portion of human vein suspended within cylinder of physiologic saline prior to insertion of laser fiber and subsequent laser treatment of Experiment #4.
FIG. 27B shows a portion of human vein that has been filled with porcine blood and the laser fiber has been inserted of Experiment #4.

FIG. 27A is a photograph of the experimental setup in which a portion of human vein was suspended within a cylinder of physiologic saline prior to insertion of laser fiber and subsequent laser treatment.

FIG. 27B is a photograph of the experimental setup in which a portion of human vein was filled with porcine blood and a fiber optic laser delivery device inserted. The fiber is connected to an automatic pullback device. The light shows where the laser tip is within the portion of vein.

The following matrix identifies the 6 different wavelengths and types of lasers used, the power at which they were operated, the rates of pullback and fiber configurations.

TABLE

| Laser and Fiber Matrix for Experiment #4. | | | | | |
|---|---|---|---|---|---|
| Laser: | No. | System Type | Power* | Pullback Rate | Fiber Configuration |
| 1320 nm Pulsed | 1 | Nd:YAG | 7 watts | 1 mm/sec | 600 um Standard Tip |
| 1310 nm CW | 2 | Diode | 7 watts | 1 mm/sec | 600 um Standard Tip |
| 810 nm CW | 3 | Diode | 7 watts | 1 mm/sec | 600 um Protected Tip |
| 810 nm CW | 4 | Diode | 7 watts | 1 mm/sec | 365 um Standard Tip |
| 1470 nm CW | 5 | Diode | 7 watts | 1 mm/sec | 600 um Standard Tip |
| 2100 nm Pulsed | 6 | Ho:YAG | 7 watts | 1 mm/sec | 600 um Standard Tip |

It will be noted that the laser used in Experiment #4 was adjusted to deliver 7 watts using a Molectron power meter.

Figure 28C:
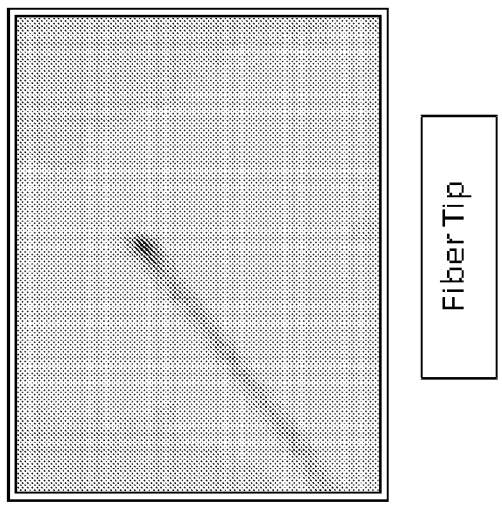
FIG. 28C shows the fiber tip after the experiment.
Figure 28B:
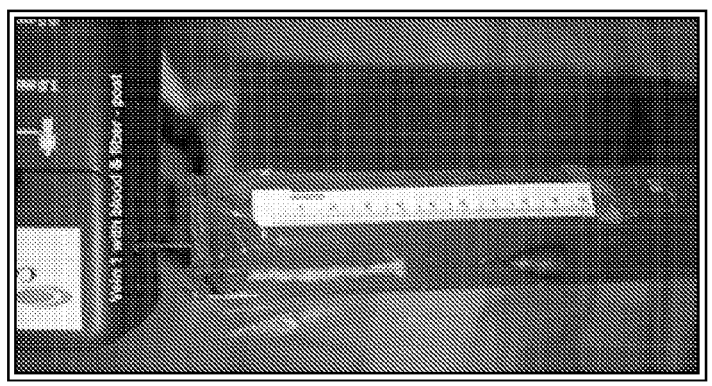
FIGS. 28A and 28B show portions of human vein suspended within cylinder of physiologic saline prior and post laser treatment using 1320 nm Nd:YAG pulsed laser.
Figure 28A:
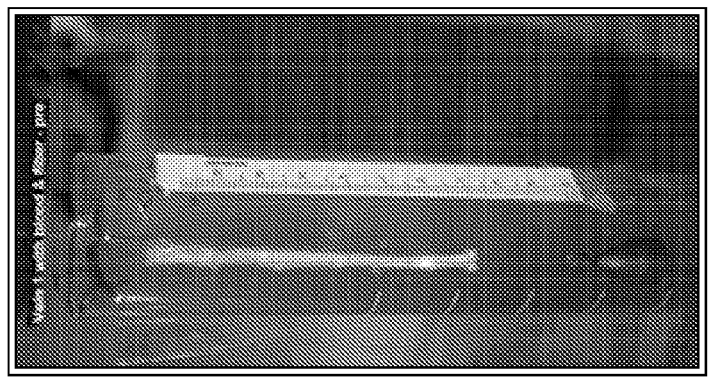

Macroscopic Results:

FIGS. 28A-28C show the experimental macroscopic results obtained using Fiber #1. The 1320 nm Nd:YAG pulsed laser was used with two portions of veins treated. Treatment yielded shrinkage of the vessel with no visible perforations and no accumulation of coagulum on the fiber tip.

Figure 29C:
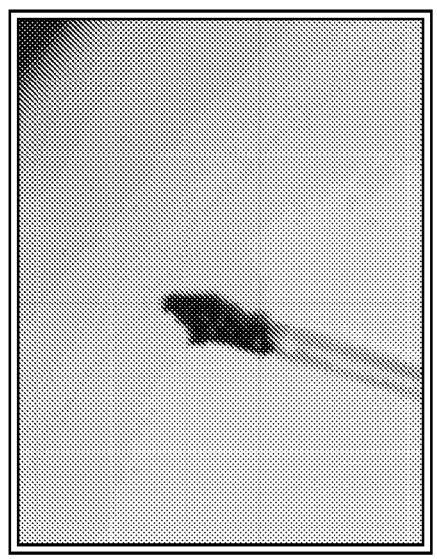
FIG. 29C shows the fiber tip after the experiment.
Figure 29B:
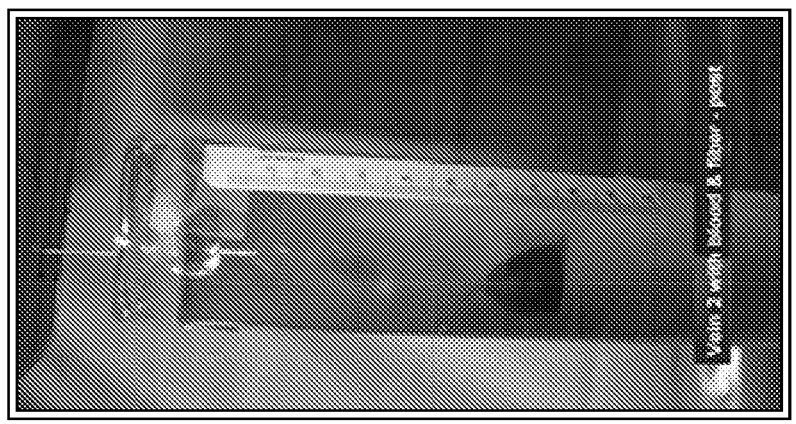
FIGS. 29A and 29B show portions of human vein suspended within cylinder of physiologic saline prior and post laser treatment using 1310 nm diode CW laser.
Figure 29A:
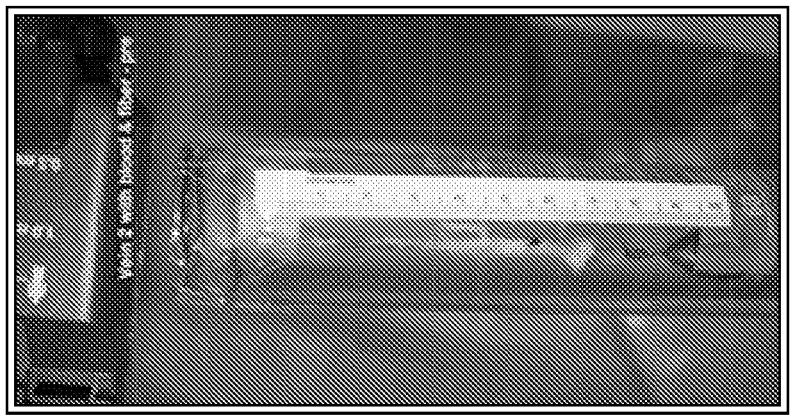

FIGS. 29A-29C show the experimental macroscopic results obtained using Fiber #2. The 1310 nm diode CW laser used caused vein shrinkage, but also caused dramatic perforations in the vessel wall.

Figure 30C:
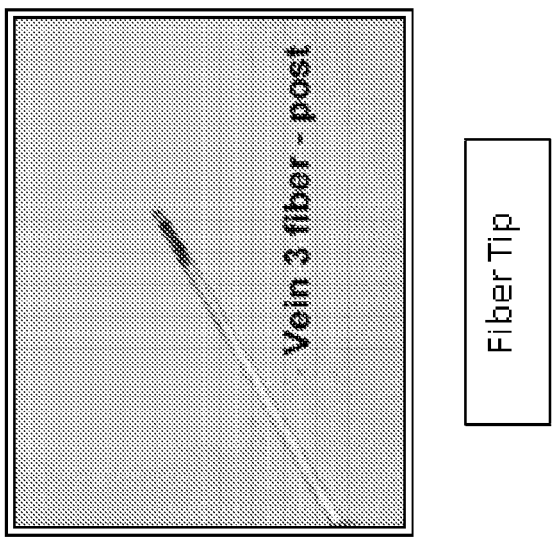
FIG. 30C shows the fiber tip after the experiment.
Figure 30B:
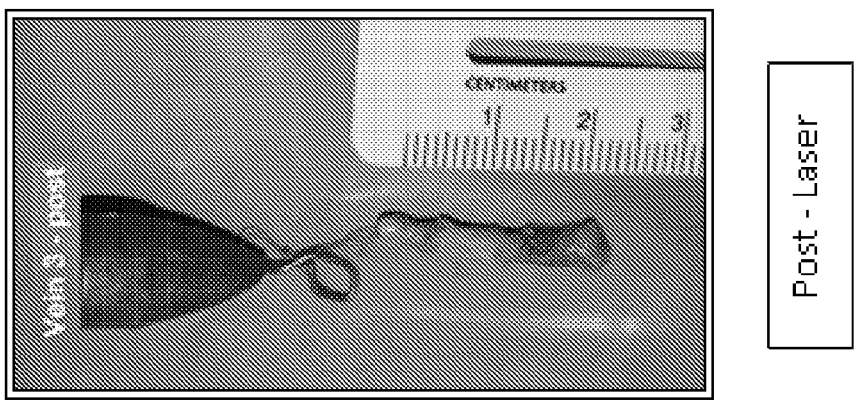
FIGS. 30A and 30B show portions O of human vein suspended within cylinder of physiologic saline prior and post laser treatment using 810 nm diode CW laser with protected tip fiber.
Figure 30A:
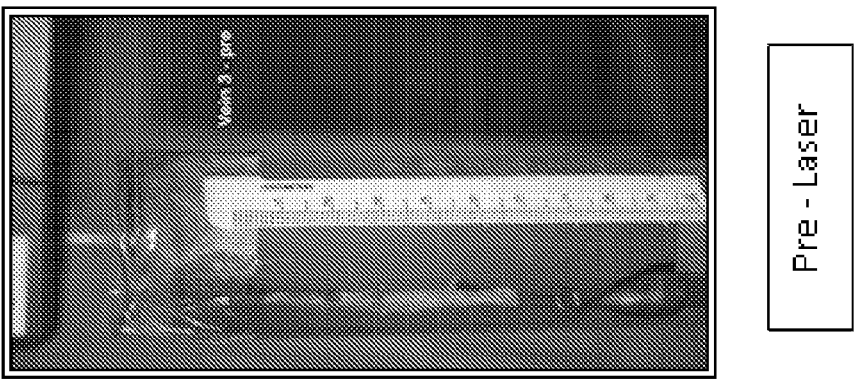

FIGS. 30A-30C show the experimental macroscopic results obtained using Fiber #3. The 810 nm diode CW laser used with the protected tip fiber yielded vein shrinkage without perforations in the vessel wall or coagulum formation on the firing tip of the fiber.

Figure 31C:
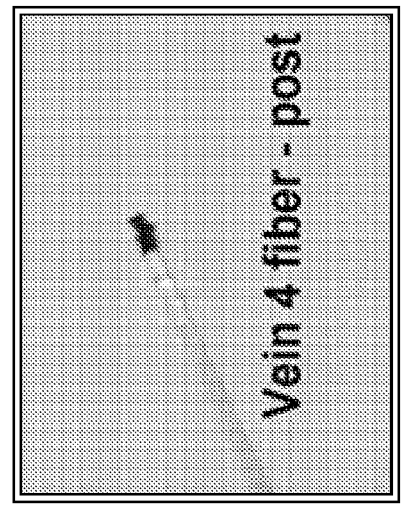
FIG. 31C shows the fiber tip after the experiment.
Figure 31B:
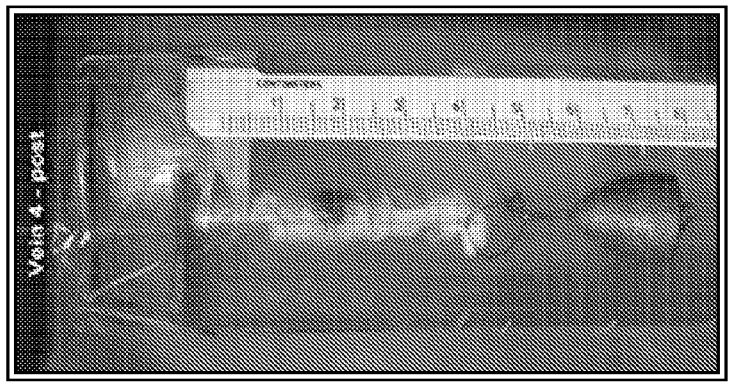
FIGS. 31A and 31B show portions of human vein suspended within cylinder of physiologic saline prior and post laser treatment using 810 nm diode CW laser with non-protected tip fiber.
Figure 31A:
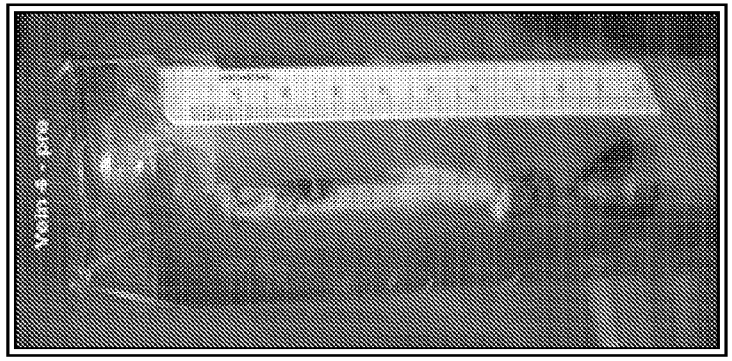

FIGS. 31A-31C show the experimental macroscopic results obtained using Fiber #4. The 810 nm diode CW laser used with a non-protected tip fiber optic laser delivery device yielded grossly discernable perforations in the vessel wall and coagulum on the tip of the fiber.

FIGS. 32A-32B show the experimental macroscopic results obtained using Fiber #5. Use of the 1470 nm diode CW laser created loud popping sounds. The optical fiber appeared to stick to the vein wall, dragging it along by its site of initial contact via the rate set by the pull-back device. Also, coagulum formed on the fiber tip.

FIGS. 33A-33B show the experimental macroscopic results obtained using Fiber #6. Again, operating the 2100 nm diode CW laser created loud popping sounds. The fiber appeared to stick to the vein wall, dragging it along by its site of initial contact via the rate set by the pull-back device. Again, coagulum also formed on the fiber tip.

Microscopic Results:

The following matrix shows the microscopic results obtained experimentally. The table identifies the wavelength and type of laser used, the total number of cross-sections of portions of vessel evaluated, the extent of thermal damage observed, and the extent of perforation or full thickness necrosis of a portion of the vein wall in terms of the number of sections where a finding of perforation or necrosis is observed divided by the total number of vessel cross-sections evaluated. A control (untreated portion of vein) counterpart from the same patient was analyzed histologically. Cross-sections of vessels treated with each laser fiber combination (as well as corresponding non-treated controls) were viewed and interpreted by a histopathologist who remained blind as to the laser used.

TABLE

Microscopic results of Experiment #4

| Laser | No. | Total # cross-sections evaluated | Thermal damage | Perforation or full thickness necrosis of a portion of the vein wall (# sections where finding is observed/total # cross-sections) |
|---|---|---|---|---|
| 1320 nm pulsed | 1 | 13 | PT, FT, AD | 2/13 (15%) |
|  |  | 13 | 0 | 0 (0%) |
| 1310 nm diode | 2 | 11 | PT, FT, AD | 7/11 (64%) |
|  |  | 11 | 0 | 0 (0%) |
| 810 nm diode protected tip | 3 | 11 | PT | 0 (0%) |
|  |  | 7 | 0 | 0 (0%) |
| 810 nm diode non-protected tip | 4 | 11 | PT, FT, AD (AD focally near perforations) | 5/11 (45%) |
|  |  | 8 | 0 | 0 (0%) |
| 1470 nm diode | 5 | 6 | PT, FT, AD | 4/6 (67%) |
|  |  | 14 | 0 | 0 (0%) |
| 2100 nm holmium | 6 | 10 | PT, FT, AD | 5/10 (50%) |
|  |  | 10 | 0 | 0 (0%) |
| 1320 nm pulsed (redo) | 1 | 9 | PT, FT, AD | 1/9 (11%) |
|  |  | 11 | 0 | 0 (0%) |

It will be noted that with regard to the microscopic results of Experiment #4, "thermal damage" is characterized by a presence of amorphous amphophilic material and/or coagulation necrosis, affecting the partial thickness of media with intervening muscle cell nuclei still visible ("PT"), affecting the full thickness of media with intervening muscle cell nuclei still visible ("FT"), and/or affecting the advential dermis ("AD"). Thermal damage is expressed in terms of the number of vessel sections where a finding is observed divided by the total number of cross-sections evaluated.

It will further be noted that the term "perforation" refers to a channel or absence of tissue in a portion of the vein wall. Full thickness necrosis of a portion of the vein wall is present when muscle cell nuclei are not visible and are replaced by coagulation necrosis and amorphous basophilic material. Again, the degree of "perforation or full thickness necrosis" refers to the number of vessel sections where the finding is observed divided by the total number of vessel cross-sections evaluated.

Conclusions:

The delivery mode, pulsed Nd:YAG vs. continuous wave diode may be just as important as the wavelength when lasers are used in an endovenous ablation procedure. Thus, the 1310 nm CW laser may NOT be equivalent to the 1320 nm pulsed laser Pulsing the laser output may dislodge any coagulum from forming on the fiber tip. This could prevent high tip temperatures, which are more likely to cause wall perforations Protected tip 810 nm fibers may be less likely to yield wall perforations than their non-protected counterparts.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for endovenous ablation of varicose veins in which thermally induced thrombus is reduced, the method comprising the following steps:
    removing blood from the varicose vein prior to treating the vein with energy using a method selected from the group consisting of elevation, external compression, massage, cooling, tumescent anesthesia, inducing spasms to the leg and suction of the vein;
    introducing an optical fiber laser deliver device, with optical fiber portion having a diameter between about 50 µm and about 1000 µm and with an energy emitting tip at its distal end, into the varicosed vein to be treated;
    emitting pulsed, laser energy with sufficient energy to close and destroy varicose veins to the emitting tip of the optical fiber laser delivery device, the pulsed laser energy having a wavelength of between about 1.2 µm and about 1.8 µm and having a pulse length between about 1 µs and about 5000 µs, and being pulsed at the rate of between about 5 Hz and about 1000 Hz and having energy per pulse of between about 1 mJ and about 500 J; and
    reducing thrombus of coagulated blood which accumulates at the energy emitting tip of the fiber when the fiber is caused to emit energy in the presence of uncoagulated blood.

2. A method for endovenous ablation of varicose veins in which thermally induced thrombus is reduced, the method comprising the following steps:
    removing blood from the varicose vein prior to treating the vein with energy using a method selected from the group consisting of elevation, external compression, massage, cooling, tumescent anesthesia, inducing spasms to the leg and suction of the vein;
    introducing an optical fiber laser deliver device, with optical fiber portion having a diameter between about 50 µm and about 1000 µm and with an energy emitting tip at its distal end, into the varicosed vein to be treated;
    emitting pulsed, laser energy with sufficient energy to close and destroy varicose veins to the emitting tip of the optical fiber laser delivery device, the pulsed laser energy having a wavelength of between about 1.9 µm and about 2.2 µm and having a pulse length between about 1 µs and about 5000 µs, and being pulsed at the rate of between about 5 Hz and about 1000 Hz and having energy per pulse of between about 1 mJ and about 500 J; and
    reducing thrombus of coagulated blood which accumulates at the energy emitting tip of the fiber when the fiber is caused to emit energy in the presence of uncoagulated blood.

* * * * *